(12) United States Patent
Shelton, IV et al.

(10) Patent No.: US 7,900,805 B2
(45) Date of Patent: Mar. 8, 2011

(54) SURGICAL INSTRUMENT WITH ENHANCED BATTERY PERFORMANCE

(75) Inventors: Frederick E. Shelton, IV, New Vienna, OH (US); James R. Giordano, Milford, OH (US); Jeffrey S. Swayze, Hamilton, OH (US); Douglas J. Siebenaler, Maineville, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 752 days.

(21) Appl. No.: 11/651,785

(22) Filed: Jan. 10, 2007

(65) Prior Publication Data
US 2008/0167644 A1    Jul. 10, 2008

(51) Int. Cl.
    *A61B 17/00*    (2006.01)
(52) U.S. Cl. ............... 227/175.1; 227/175.3; 227/176.1; 227/182.1; 206/363; 206/364; 206/365; 206/701; 235/492
(58) Field of Classification Search ............... 227/175.1, 227/175.3, 176.1, 182.1; 206/438, 363–365, 206/701; 235/492; 53/492
    See application file for complete search history.

(56) References Cited

U.S. PATENT DOCUMENTS

| | | | |
|---|---|---|---|
| 3,490,675 A | 1/1970 | Green et al. |
| 3,643,851 A | 2/1972 | Green et al. |
| 3,662,939 A | 5/1972 | Bryan |
| 3,717,294 A | 2/1973 | Green |
| 3,819,100 A | 6/1974 | Noiles et al. |
| 4,331,277 A | 5/1982 | Green |
| 4,383,634 A | 5/1983 | Green |
| 4,396,139 A | 8/1983 | Hall et al. |
| 4,402,445 A | 9/1983 | Green |
| 4,415,112 A | 11/1983 | Green |
| 4,429,695 A | 2/1984 | Green |
| 4,475,679 A | 10/1984 | Fleury, Jr. |
| 4,489,875 A | 12/1984 | Crawford et al. |
| 4,500,024 A | 2/1985 | DiGiovanni et al. |
| 4,505,273 A | 3/1985 | Braun et al. |
| 4,505,414 A | 3/1985 | Filipi |
| 4,506,671 A | 3/1985 | Green |
| 4,522,327 A | 6/1985 | Korthoff et al. |
| 4,530,453 A | 7/1985 | Green |
| 4,566,620 A | 1/1986 | Green et al. |
| 4,573,622 A | 3/1986 | Green et al. |

(Continued)

FOREIGN PATENT DOCUMENTS

CA    2458946 A1    3/2003

(Continued)

OTHER PUBLICATIONS

European Search Report, Application No. 08250099.2, dated Jul. 9, 2008 (1 page).

(Continued)

*Primary Examiner* — Rinaldi I. Rada
*Assistant Examiner* — Michelle Lopez

(57) ABSTRACT

An assembly including a component of a surgical instrument, such as an endoscopic or laparoscopic instrument. The assembly may comprise a package; a surgical instrument component within the package; and a power source within the package. The power source may be configured to be placed in electrical communication with the surgical instrument component. The assembly may also comprise an auxiliary power source within the package and a circuit element, where the circuit element is in electrical communication with the power source and the auxiliary power source.

17 Claims, 18 Drawing Sheets

U.S. PATENT DOCUMENTS

| | | |
|---|---|---|
| 4,580,712 A | 4/1986 | Green |
| 4,610,383 A | 9/1986 | Rothfuss et al. |
| 4,629,107 A | 12/1986 | Fedotov et al. |
| 4,641,076 A * | 2/1987 | Linden .......................... 320/113 |
| 4,655,222 A | 4/1987 | Florez et al. |
| 4,664,305 A | 5/1987 | Blake, III et al. |
| 4,671,445 A | 6/1987 | Barker et al. |
| 4,715,520 A | 12/1987 | Roehr, Jr. et al. |
| 4,728,020 A | 3/1988 | Green et al. |
| 4,752,024 A | 6/1988 | Green et al. |
| 4,754,909 A | 7/1988 | Barker et al. |
| 4,767,044 A | 8/1988 | Green |
| 4,805,823 A | 2/1989 | Rothfuss |
| 4,809,695 A | 3/1989 | Gwathmey et al. |
| 4,817,847 A | 4/1989 | Redtenbacher et al. |
| 4,819,853 A | 4/1989 | Green |
| 4,821,939 A | 4/1989 | Green |
| 4,869,414 A | 9/1989 | Green et al. |
| 4,869,415 A | 9/1989 | Fox |
| 4,941,623 A | 7/1990 | Pruitt |
| 4,944,443 A | 7/1990 | Oddsen et al. |
| 5,065,929 A | 11/1991 | Schulze et al. |
| 5,071,430 A | 12/1991 | de Salis et al. |
| 5,129,570 A | 7/1992 | Schulze et al. |
| 5,137,198 A | 8/1992 | Nobis et al. |
| 5,139,513 A | 8/1992 | Segato |
| 5,158,567 A | 10/1992 | Green |
| 5,211,649 A | 5/1993 | Kohler et al. |
| 5,221,036 A | 6/1993 | Takase |
| 5,222,975 A | 6/1993 | Crainich |
| 5,258,009 A | 11/1993 | Conners |
| 5,282,806 A | 2/1994 | Haber et al. |
| 5,282,829 A | 2/1994 | Hermes |
| 5,304,204 A | 4/1994 | Bregen |
| 5,342,395 A | 8/1994 | Jarrett et al. |
| 5,342,396 A | 8/1994 | Cook |
| 5,350,400 A | 9/1994 | Esposito et al. |
| 5,356,006 A * | 10/1994 | Alpern et al. .................. 206/363 |
| 5,366,479 A | 11/1994 | McGarry et al. |
| 5,383,880 A | 1/1995 | Hooven |
| 5,395,033 A * | 3/1995 | Byrne et al. ................. 227/175.1 |
| 5,397,324 A | 3/1995 | Carroll et al. |
| 5,413,272 A | 5/1995 | Green et al. |
| 5,417,361 A | 5/1995 | Williamson, IV |
| 5,425,745 A | 6/1995 | Green et al. |
| 5,433,721 A | 7/1995 | Hooven et al. |
| 5,465,895 A | 11/1995 | Knodel et al. |
| 5,474,566 A | 12/1995 | Alesi et al. |
| 5,478,354 A | 12/1995 | Tovey et al. |
| 5,480,089 A | 1/1996 | Blewett |
| 5,484,095 A | 1/1996 | Green et al. |
| 5,484,451 A | 1/1996 | Akopov et al. |
| 5,485,947 A | 1/1996 | Olson et al. |
| 5,487,499 A | 1/1996 | Sorrentino et al. |
| 5,487,500 A | 1/1996 | Knodel et al. |
| 5,489,058 A | 2/1996 | Plyley et al. |
| 5,497,933 A | 3/1996 | DeFonzo et al. |
| 5,503,320 A | 4/1996 | Webster et al. |
| 5,509,596 A | 4/1996 | Green et al. |
| 5,518,163 A | 5/1996 | Hooven |
| 5,518,164 A | 5/1996 | Hooven |
| 5,529,235 A | 6/1996 | Boiarski et al. |
| 5,535,934 A | 7/1996 | Boiarski et al. |
| 5,535,937 A | 7/1996 | Boiarski et al. |
| 5,543,119 A | 8/1996 | Sutter et al. |
| 5,553,765 A | 9/1996 | Knodel et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,239 A * | 10/1996 | Boiarski et al. ............ 227/175.2 |
| 5,562,241 A | 10/1996 | Knodel et al. |
| 5,562,682 A | 10/1996 | Oberlin et al. |
| 5,564,615 A | 10/1996 | Bishop et al. |
| 5,571,116 A | 11/1996 | Bolanos et al. |
| 5,575,799 A | 11/1996 | Bolanos et al. |
| 5,577,654 A | 11/1996 | Bishop |
| 5,579,978 A | 12/1996 | Green et al. |
| 5,580,067 A | 12/1996 | Hamblin et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,601,224 A | 2/1997 | Bishop et al. |
| 5,605,273 A | 2/1997 | Hamblin et al. |
| 5,607,094 A | 3/1997 | Clark et al. |
| 5,609,285 A | 3/1997 | Grant et al. |
| 5,624,452 A * | 4/1997 | Yates ............................. 606/139 |
| 5,628,446 A | 5/1997 | Geiste et al. |
| 5,630,539 A | 5/1997 | Plyley et al. |
| 5,630,540 A | 5/1997 | Blewett |
| 5,632,432 A | 5/1997 | Schulze et al. |
| 5,632,433 A | 5/1997 | Grant et al. |
| 5,634,584 A | 6/1997 | Okorocha et al. |
| 5,636,780 A | 6/1997 | Green et al. |
| 5,639,008 A | 6/1997 | Gallagher et al. |
| 5,649,937 A | 7/1997 | Bito et al. |
| 5,651,491 A | 7/1997 | Heaton et al. |
| 5,653,373 A | 8/1997 | Green et al. |
| 5,653,374 A | 8/1997 | Young et al. |
| 5,653,677 A | 8/1997 | Okada et al. |
| 5,655,698 A | 8/1997 | Yoon |
| 5,657,921 A | 8/1997 | Young et al. |
| 5,658,300 A | 8/1997 | Bito et al. |
| 5,662,258 A | 9/1997 | Knodel et al. |
| 5,662,260 A | 9/1997 | Yoon |
| 5,667,517 A * | 9/1997 | Hooven ......................... 606/151 |
| 5,667,527 A | 9/1997 | Cook |
| 5,669,544 A | 9/1997 | Schulze et al. |
| 5,673,840 A | 10/1997 | Schulze et al. |
| 5,673,841 A | 10/1997 | Schulze et al. |
| 5,680,981 A | 10/1997 | Mililli et al. |
| 5,680,982 A | 10/1997 | Schulze et al. |
| 5,680,983 A | 10/1997 | Plyley et al. |
| 5,685,474 A | 11/1997 | Seeber |
| 5,688,270 A | 11/1997 | Yates et al. |
| 5,690,269 A | 11/1997 | Bolanos et al. |
| 5,692,668 A | 12/1997 | Schulze et al. |
| 5,693,042 A | 12/1997 | Boiarski et al. |
| 5,697,543 A | 12/1997 | Burdorff |
| 5,702,408 A | 12/1997 | Wales et al. |
| 5,704,087 A * | 1/1998 | Strub ............................... 15/105 |
| 5,704,534 A | 1/1998 | Huitema et al. |
| 5,706,998 A | 1/1998 | Plyley et al. |
| 5,709,334 A | 1/1998 | Sorrentino et al. |
| 5,709,680 A | 1/1998 | Yates et al. |
| 5,711,472 A | 1/1998 | Bryan |
| 5,713,505 A | 2/1998 | Huitema |
| 5,715,987 A | 2/1998 | Kelley et al. |
| 5,716,366 A | 2/1998 | Yates |
| 5,718,360 A | 2/1998 | Green et al. |
| 5,725,536 A | 3/1998 | Oberlin et al. |
| 5,725,554 A | 3/1998 | Simon et al. |
| 5,730,758 A | 3/1998 | Allgeyer |
| 5,732,871 A | 3/1998 | Clark et al. |
| 5,732,872 A | 3/1998 | Bolduc et al. |
| 5,743,456 A | 4/1998 | Jones et al. |
| 5,752,644 A | 5/1998 | Bolanos et al. |
| 5,758,814 A | 6/1998 | Gallagher et al. |
| 5,762,256 A | 6/1998 | Mastri et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,785,232 A | 7/1998 | Vidal et al. |
| 5,797,536 A | 8/1998 | Smith et al. |
| 5,797,537 A | 8/1998 | Oberlin et al. |
| 5,797,538 A | 8/1998 | Heaton et al. |
| 5,799,857 A | 9/1998 | Robertson et al. |
| 5,807,393 A | 9/1998 | Williamson, IV et al. |
| 5,817,093 A | 10/1998 | Williamson, IV et al. |
| 5,820,009 A | 10/1998 | Melling et al. |
| 5,826,776 A | 10/1998 | Schulze et al. |
| 5,833,695 A | 11/1998 | Yoon |
| 5,836,503 A | 11/1998 | Ehrenfels et al. |
| 5,839,639 A | 11/1998 | Sauer et al. |
| 5,855,311 A | 1/1999 | Hamblin et al. |

| | | | |
|---|---|---|---|
| 5,865,361 A | 2/1999 | Milliman et al. | |
| 5,868,760 A | 2/1999 | McGuckin, Jr. | |
| 5,876,401 A * | 3/1999 | Schulze et al. ............... 606/51 | |
| 5,893,506 A | 4/1999 | Powell | |
| 5,897,562 A | 4/1999 | Bolanos et al. | |
| 5,901,895 A | 5/1999 | Heaton et al. | |
| 5,908,427 A | 6/1999 | McKean et al. | |
| 5,911,353 A | 6/1999 | Bolanos et al. | |
| 5,915,616 A | 6/1999 | Viola et al. | |
| 5,918,791 A | 7/1999 | Sorrentino et al. | |
| 5,919,198 A | 7/1999 | Graves, Jr. et al. | |
| 5,941,442 A | 8/1999 | Geiste et al. | |
| 5,954,259 A | 9/1999 | Viola et al. | |
| 6,010,054 A | 1/2000 | Johnson et al. | |
| 6,024,741 A | 2/2000 | Williamson, IV et al. | |
| 6,032,849 A | 3/2000 | Mastri et al. | |
| 6,045,560 A | 4/2000 | McKean et al. | |
| 6,083,242 A | 7/2000 | Cook | |
| 6,086,600 A | 7/2000 | Kortenbach | |
| 6,099,551 A | 8/2000 | Gabbay | |
| 6,102,271 A | 8/2000 | Longo et al. | |
| 6,119,913 A | 9/2000 | Adams et al. | |
| 6,126,058 A | 10/2000 | Adams et al. | |
| 6,171,330 B1 | 1/2001 | Benchetrit | |
| 6,181,105 B1 * | 1/2001 | Cutolo et al. ............... 320/115 | |
| 6,202,914 B1 | 3/2001 | Geiste et al. | |
| 6,241,139 B1 | 6/2001 | Milliman et al. | |
| 6,250,532 B1 | 6/2001 | Green et al. | |
| 6,264,086 B1 | 7/2001 | McGuckin, Jr. | |
| 6,264,087 B1 | 7/2001 | Whitman | |
| 6,273,897 B1 | 8/2001 | Dalessandro et al. | |
| 6,302,311 B1 | 10/2001 | Adams et al. | |
| 6,315,184 B1 | 11/2001 | Whitman | |
| 6,330,965 B1 | 12/2001 | Milliman et al. | |
| 6,346,077 B1 | 2/2002 | Taylor et al. | |
| 6,387,113 B1 | 5/2002 | Hawkins et al. | |
| RE37,814 E | 8/2002 | Allgeyer | |
| 6,436,107 B1 | 8/2002 | Wang et al. | |
| 6,443,973 B1 | 9/2002 | Whitman | |
| 6,488,197 B1 | 12/2002 | Whitman | |
| 6,491,201 B1 | 12/2002 | Whitman | |
| 6,505,768 B2 | 1/2003 | Whitman | |
| 6,517,565 B1 | 2/2003 | Whitman et al. | |
| 6,578,751 B2 | 6/2003 | Hartwick | |
| 6,588,643 B2 | 7/2003 | Bolduc et al. | |
| 6,596,432 B2 * | 7/2003 | Kawakami et al. ............. 429/60 | |
| 6,601,749 B2 | 8/2003 | Sullivan et al. | |
| 6,616,686 B2 | 9/2003 | Coleman et al. | |
| 6,619,529 B2 | 9/2003 | Green et al. | |
| 6,629,988 B2 | 10/2003 | Weadock | |
| 6,644,532 B2 | 11/2003 | Green et al. | |
| 6,648,816 B2 | 11/2003 | Irion et al. | |
| 6,666,875 B1 * | 12/2003 | Sakurai et al. ............... 606/169 | |
| 6,679,410 B2 | 1/2004 | Würsch et al. | |
| 6,681,978 B2 | 1/2004 | Geiste et al. | |
| 6,681,979 B2 | 1/2004 | Whitman | |
| 6,695,199 B2 | 2/2004 | Whitman | |
| 6,698,643 B2 | 3/2004 | Whitman | |
| 6,716,233 B1 | 4/2004 | Whitman | |
| 6,755,338 B2 | 6/2004 | Hahnen et al. | |
| 6,769,594 B2 | 8/2004 | Orban, III | |
| 6,773,438 B1 | 8/2004 | Knodel et al. | |
| 6,793,652 B1 | 9/2004 | Whitman et al. | |
| 6,805,273 B2 | 10/2004 | Bilotti et al. | |
| 6,817,508 B1 | 11/2004 | Racenet et al. | |
| 6,817,509 B2 | 11/2004 | Geiste et al. | |
| 6,830,174 B2 | 12/2004 | Hillstead et al. | |
| 6,843,403 B2 | 1/2005 | Whitman | |
| 6,846,307 B2 | 1/2005 | Whitman et al. | |
| 6,846,308 B2 | 1/2005 | Whitman et al. | |
| 6,846,309 B2 | 1/2005 | Whitman et al. | |
| 6,849,071 B2 | 2/2005 | Whitman et al. | |
| RE38,708 E | 3/2005 | Bolanos et al. | |
| 6,874,669 B2 | 4/2005 | Adams et al. | |
| 6,877,647 B2 | 4/2005 | Green et al. | |
| 6,905,057 B2 | 6/2005 | Swayze et al. | |
| 6,945,444 B2 | 9/2005 | Gresham et al. | |
| 6,953,138 B1 | 10/2005 | Dworak et al. | |
| 6,953,139 B2 | 10/2005 | Milliman et al. | |
| 6,959,852 B2 | 11/2005 | Shelton, IV et al. | |
| 6,964,363 B2 | 11/2005 | Wales et al. | |
| 6,978,921 B2 | 12/2005 | Shelton, IV et al. | |
| 6,978,922 B2 | 12/2005 | Bilotti et al. | |
| 6,981,628 B2 | 1/2006 | Wales | |
| 6,981,941 B2 | 1/2006 | Whitman et al. | |
| 6,986,451 B1 | 1/2006 | Mastri et al. | |
| 6,988,649 B2 | 1/2006 | Shelton, IV et al. | |
| 6,988,650 B2 | 1/2006 | Schwemberger et al. | |
| 7,000,818 B2 | 2/2006 | Shelton, IV et al. | |
| 7,000,819 B2 | 2/2006 | Swayze et al. | |
| 7,008,435 B2 | 3/2006 | Cummins | |
| 7,025,743 B2 | 4/2006 | Mann et al. | |
| 7,032,798 B2 | 4/2006 | Whitman et al. | |
| 7,032,799 B2 | 4/2006 | Viola et al. | |
| 7,044,352 B2 | 5/2006 | Shelton, IV et al. | |
| 7,044,353 B2 | 5/2006 | Mastri et al. | |
| 7,055,731 B2 | 6/2006 | Shelton, IV et al. | |
| 7,056,330 B2 | 6/2006 | Gayton | |
| 7,070,083 B2 | 7/2006 | Jankowski | |
| 7,077,856 B2 | 7/2006 | Whitman | |
| 7,080,769 B2 | 7/2006 | Vresh et al. | |
| 7,083,075 B2 | 8/2006 | Swayze et al. | |
| 7,083,571 B2 | 8/2006 | Wang et al. | |
| 7,090,684 B2 | 8/2006 | McGuckin, Jr. et al. | |
| 7,108,695 B2 | 9/2006 | Witt et al. | |
| 7,108,709 B2 | 9/2006 | Cummins | |
| 7,111,769 B2 | 9/2006 | Wales et al. | |
| 7,114,642 B2 | 10/2006 | Whitman | |
| 7,118,582 B1 | 10/2006 | Wang et al. | |
| 7,121,446 B2 | 10/2006 | Arad et al. | |
| 7,128,253 B2 | 10/2006 | Mastri et al. | |
| 7,128,254 B2 | 10/2006 | Shelton, IV et al. | |
| 7,140,527 B2 | 11/2006 | Ehrenfels et al. | |
| 7,147,138 B2 | 12/2006 | Shelton, IV | |
| 7,159,750 B2 | 1/2007 | Racenet et al. | |
| 7,168,604 B2 | 1/2007 | Milliman et al. | |
| 7,188,758 B2 | 3/2007 | Viola et al. | |
| 7,207,471 B2 | 4/2007 | Heinrich et al. | |
| 7,207,472 B2 | 4/2007 | Wukusick et al. | |
| 7,210,609 B2 | 5/2007 | Leiboff et al. | |
| 7,213,736 B2 | 5/2007 | Wales et al. | |
| 7,220,272 B2 | 5/2007 | Weadock | |
| 7,225,964 B2 | 6/2007 | Mastri et al. | |
| 7,238,195 B2 | 7/2007 | Viola | |
| 7,246,734 B2 | 7/2007 | Shelton, IV | |
| 7,258,262 B2 | 8/2007 | Mastri et al. | |
| 7,260,431 B2 | 8/2007 | Libbus et al. | |
| 7,278,562 B2 | 10/2007 | Mastri et al. | |
| 7,278,563 B1 | 10/2007 | Green | |
| 7,296,724 B2 | 11/2007 | Green et al. | |
| 7,303,106 B2 | 12/2007 | Milliman et al. | |
| 7,303,107 B2 | 12/2007 | Milliman et al. | |
| 7,303,108 B2 | 12/2007 | Shelton, IV | |
| 7,303,556 B2 | 12/2007 | Metzger | |
| 7,328,828 B2 | 2/2008 | Ortiz et al. | |
| 7,328,829 B2 | 2/2008 | Arad et al. | |
| 7,354,447 B2 | 4/2008 | Shelton, IV et al. | |
| 7,364,061 B2 | 4/2008 | Swayze et al. | |
| 7,380,695 B2 | 6/2008 | Doll et al. | |
| 7,380,696 B2 | 6/2008 | Shelton, IV et al. | |
| 7,398,907 B2 | 7/2008 | Racenet et al. | |
| 7,398,908 B2 | 7/2008 | Holsten et al. | |
| 7,404,508 B2 | 7/2008 | Smith et al. | |
| 7,404,509 B2 | 7/2008 | Ortiz et al. | |
| 7,407,075 B2 | 8/2008 | Holsten et al. | |
| 7,407,078 B2 | 8/2008 | Shelton, IV et al. | |
| 7,410,086 B2 | 8/2008 | Ortiz et al. | |
| 7,416,101 B2 | 8/2008 | Shelton, IV et al. | |
| 7,422,136 B1 | 9/2008 | Marczyk | |
| 7,422,139 B2 | 9/2008 | Shelton, IV et al. | |
| 7,424,965 B2 | 9/2008 | Racenet et al. | |
| 7,431,188 B1 | 10/2008 | Marczyk | |
| 7,431,189 B2 | 10/2008 | Shelton, IV et al. | |
| 7,431,730 B2 | 10/2008 | Viola | |
| 7,434,717 B2 | 10/2008 | Shelton, IV et al. | |
| 7,438,209 B1 | 10/2008 | Hess et al. | |
| 7,441,684 B2 | 10/2008 | Shelton, IV et al. | |
| 7,441,685 B1 | 10/2008 | Boudreaux | |

| | | |
|---|---|---|
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,467,740 B2 | 12/2008 | Shelton, IV et al. |
| 7,472,815 B2 | 1/2009 | Shelton, IV et al. |
| 7,481,347 B2 | 1/2009 | Roy |
| 7,490,749 B2 | 2/2009 | Schall et al. |
| 7,494,039 B2 | 2/2009 | Racenet et al. |
| 7,500,979 B2 | 3/2009 | Hueil et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,546,940 B2 | 6/2009 | Milliman et al. |
| 7,631,793 B2 | 12/2009 | Rethy et al. |
| 7,665,646 B2 | 2/2010 | Prommersberger |
| 2002/0117534 A1 | 8/2002 | Green et al. |
| 2003/0093103 A1 | 5/2003 | Malackowski et al. |
| 2003/0105478 A1 | 6/2003 | Whitman et al. |
| 2003/0130677 A1 | 7/2003 | Whitman et al. |
| 2004/0006372 A1 | 1/2004 | Racenet et al. |
| 2004/0034369 A1 | 2/2004 | Sauer et al. |
| 2004/0094597 A1 | 5/2004 | Whitman et al. |
| 2004/0108357 A1 | 6/2004 | Milliman et al. |
| 2004/0116952 A1 | 6/2004 | Sakurai et al. |
| 2004/0164123 A1 | 8/2004 | Racenet et al. |
| 2004/0167572 A1 | 8/2004 | Roth et al. |
| 2004/0173659 A1 | 9/2004 | Green et al. |
| 2004/0222268 A1 | 11/2004 | Bilotti et al. |
| 2004/0232201 A1 | 11/2004 | Wenchell et al. |
| 2004/0243151 A1 | 12/2004 | Demmy et al. |
| 2004/0254608 A1 | 12/2004 | Huitema et al. |
| 2005/0032511 A1 | 2/2005 | Malone et al. |
| 2005/0059997 A1 | 3/2005 | Bauman et al. |
| 2005/0103819 A1 | 5/2005 | Racenet et al. |
| 2005/0119669 A1 | 6/2005 | Demmy |
| 2005/0125009 A1 | 6/2005 | Perry et al. |
| 2005/0131390 A1 | 6/2005 | Heinrich et al. |
| 2005/0143759 A1 | 6/2005 | Kelly |
| 2005/0184121 A1 | 8/2005 | Heinrich |
| 2005/0187576 A1 | 8/2005 | Whitman et al. |
| 2005/0189397 A1 | 9/2005 | Jankowski |
| 2005/0192628 A1 | 9/2005 | Viola |
| 2005/0216055 A1 | 9/2005 | Scirica et al. |
| 2005/0240222 A1 | 10/2005 | Shipp |
| 2005/0263563 A1 | 12/2005 | Racenet et al. |
| 2005/0274768 A1 | 12/2005 | Cummins et al. |
| 2006/0011699 A1 | 1/2006 | Olson et al. |
| 2006/0025812 A1 | 2/2006 | Shelton, IV |
| 2006/0047307 A1 | 3/2006 | Ortiz et al. |
| 2006/0049229 A1 | 3/2006 | Milliman et al. |
| 2006/0052825 A1 | 3/2006 | Ransick et al. |
| 2006/0085033 A1 | 4/2006 | Criscuolo et al. |
| 2006/0100643 A1 | 5/2006 | Laufer et al. |
| 2006/0108393 A1 | 5/2006 | Heinrich et al. |
| 2006/0180634 A1 | 8/2006 | Shelton, IV et al. |
| 2006/0212069 A1 | 9/2006 | Shelton, IV |
| 2006/0226196 A1 | 10/2006 | Hueil et al. |
| 2006/0235469 A1 | 10/2006 | Viola |
| 2006/0241692 A1 | 10/2006 | McGuckin, Jr. et al. |
| 2006/0273135 A1 | 12/2006 | Beetel |
| 2006/0278680 A1 | 12/2006 | Viola et al. |
| 2006/0278681 A1 | 12/2006 | Viola et al. |
| 2006/0289602 A1 | 12/2006 | Wales et al. |
| 2007/0023476 A1 | 2/2007 | Whitman et al. |
| 2007/0023477 A1 | 2/2007 | Whitman et al. |
| 2007/0034668 A1 | 2/2007 | Holsten et al. |
| 2007/0045379 A1 | 3/2007 | Shelton, IV |
| 2007/0073341 A1 | 3/2007 | Smith |
| 2007/0084897 A1 | 4/2007 | Shelton, IV et al. |
| 2007/0102452 A1 | 5/2007 | Shelton, IV et al. |
| 2007/0102453 A1 | 5/2007 | Morgan et al. |
| 2007/0102472 A1 | 5/2007 | Shelton, IV |
| 2007/0102473 A1 | 5/2007 | Shelton, IV et al. |
| 2007/0102474 A1 | 5/2007 | Shelton, IV et al. |
| 2007/0106317 A1 | 5/2007 | Shelton, IV et al. |
| 2007/0114261 A1 | 5/2007 | Ortiz et al. |
| 2007/0158385 A1 | 7/2007 | Hueil et al. |
| 2007/0170225 A1 | 7/2007 | Shelton, IV et al. |
| 2007/0173806 A1 | 7/2007 | Orszulak et al. |
| 2007/0173813 A1 | 7/2007 | Odom |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175953 A1 | 8/2007 | Shelton, IV et al. |
| 2007/0175955 A1 | 8/2007 | Shelton, IV et al. |
| 2007/0175956 A1 | 8/2007 | Swayze et al. |
| 2007/0175957 A1 | 8/2007 | Shelton, IV et al. |
| 2007/0175958 A1 | 8/2007 | Shelton, IV et al. |
| 2007/0175959 A1 | 8/2007 | Shelton, IV et al. |
| 2007/0175964 A1 | 8/2007 | Shelton, IV et al. |
| 2007/0179476 A1 | 8/2007 | Shelton, IV et al. |
| 2007/0181632 A1 | 8/2007 | Milliman |
| 2007/0194079 A1 | 8/2007 | Hueil et al. |
| 2007/0194080 A1 | 8/2007 | Swayze et al. |
| 2007/0194081 A1 | 8/2007 | Hueil et al. |
| 2007/0194082 A1 | 8/2007 | Morgan et al. |
| 2007/0233053 A1 | 10/2007 | Shelton, IV et al. |
| 2007/0246505 A1 | 10/2007 | Pace-Floridia et al. |
| 2007/0295780 A1 | 12/2007 | Shelton et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0029576 A1 | 2/2008 | Shelton et al. |
| 2008/0035701 A1 | 2/2008 | Racenet et al. |
| 2008/0041917 A1 | 2/2008 | Racenet et al. |
| 2008/0078800 A1 | 4/2008 | Hess et al. |
| 2008/0078801 A1 | 4/2008 | Shelton et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078806 A1 | 4/2008 | Omaits et al. |
| 2008/0078807 A1 | 4/2008 | Hess et al. |
| 2008/0078808 A1 | 4/2008 | Hess et al. |
| 2008/0082115 A1 | 4/2008 | Morgan et al. |
| 2008/0082124 A1 | 4/2008 | Hess et al. |
| 2008/0082125 A1 | 4/2008 | Murray et al. |
| 2008/0082126 A1 | 4/2008 | Murray et al. |
| 2008/0083813 A1 | 4/2008 | Zemlok et al. |
| 2008/0140115 A1 | 6/2008 | Stopek |
| 2008/0164296 A1 | 7/2008 | Shelton et al. |
| 2008/0167522 A1 | 7/2008 | Giordano et al. |
| 2008/0167670 A1 | 7/2008 | Shelton et al. |
| 2008/0167671 A1 | 7/2008 | Giordano et al. |
| 2008/0167672 A1 | 7/2008 | Giordano et al. |
| 2008/0167736 A1 | 7/2008 | Swayze et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0197167 A1 | 8/2008 | Viola et al. |
| 2008/0210738 A1 | 9/2008 | Shelton et al. |
| 2008/0237296 A1 | 10/2008 | Boudreaux et al. |
| 2008/0251568 A1 | 10/2008 | Zemlok et al. |
| 2008/0283570 A1 | 11/2008 | Boyden et al. |
| 2008/0290134 A1 | 11/2008 | Bettuchi et al. |
| 2008/0296343 A1 | 12/2008 | Schall et al. |
| 2008/0296345 A1 | 12/2008 | Shelton, IV et al. |
| 2008/0296346 A1 | 12/2008 | Shelton, IV et al. |
| 2008/0296347 A1 | 12/2008 | Shelton, IV et al. |
| 2008/0300579 A1 | 12/2008 | Broehl et al. |
| 2008/0300580 A1 | 12/2008 | Shelton, IV et al. |
| 2008/0300613 A1 | 12/2008 | Shelton, IV et al. |
| 2008/0308601 A1 | 12/2008 | Timm et al. |
| 2008/0308602 A1 | 12/2008 | Timm et al. |
| 2008/0308603 A1 | 12/2008 | Shelton, IV et al. |
| 2008/0308606 A1 | 12/2008 | Timm et al. |
| 2008/0308607 A1 | 12/2008 | Timm et al. |
| 2008/0308608 A1 | 12/2008 | Prommersberger |
| 2008/0314954 A1 | 12/2008 | Boudreaux |
| 2008/0314955 A1 | 12/2008 | Boudreaux et al. |
| 2008/0314956 A1 | 12/2008 | Boudreaux |
| 2008/0314957 A1 | 12/2008 | Boudreaux |
| 2008/0314961 A1 | 12/2008 | Boudreaux et al. |
| 2008/0314962 A1 | 12/2008 | Boudreaux |

| | | | | | | |
|---|---|---|---|---|---|---|
| 2009/0001121 A1 | 1/2009 | Hess et al. | | EP | 0070230 B1 | 10/1985 |
| 2009/0001122 A1 | 1/2009 | Prommersberger et al. | | EP | 0033548 B1 | 5/1986 |
| 2009/0001123 A1 | 1/2009 | Morgan et al. | | EP | 0276104 A2 | 7/1988 |
| 2009/0001124 A1 | 1/2009 | Hess et al. | | EP | 0639349 A2 | 2/1994 |
| 2009/0001125 A1 | 1/2009 | Hess et al. | | EP | 0324636 B1 | 3/1994 |
| 2009/0001126 A1 | 1/2009 | Hess et al. | | EP | 0593920 A1 | 4/1994 |
| 2009/0001128 A1 | 1/2009 | Weisenburgh, II et al. | | EP | 0600182 A2 | 6/1994 |
| 2009/0001130 A1 | 1/2009 | Hess et al. | | EP | 0630612 A1 | 12/1994 |
| 2009/0005807 A1 | 1/2009 | Hess et al. | | EP | 0634144 A1 | 1/1995 |
| 2009/0005808 A1 | 1/2009 | Hess et al. | | EP | 0646356 A2 | 4/1995 |
| 2009/0005809 A1 | 1/2009 | Hess et al. | | EP | 0646357 A1 | 4/1995 |
| 2009/0012556 A1 | 1/2009 | Boudreaux et al. | | EP | 0653189 A2 | 5/1995 |
| 2009/0076534 A1 | 3/2009 | Shelton, IV et al. | | EP | 0669104 A1 | 8/1995 |
| 2009/0157067 A1 | 6/2009 | Kane et al. | | EP | 0511470 B1 | 10/1995 |
| 2009/0200355 A1 | 8/2009 | Baxter, III et al. | | EP | 0679367 A2 | 11/1995 |
| 2009/0206123 A1 | 8/2009 | Doll et al. | | EP | 0392547 B1 | 12/1995 |
| 2009/0206124 A1 | 8/2009 | Hall et al. | | EP | 0685204 A1 | 12/1995 |
| 2009/0206125 A1 | 8/2009 | Huitema et al. | | EP | 0699418 A1 | 3/1996 |
| 2009/0206126 A1 | 8/2009 | Huitema et al. | | EP | 0702937 A1 | 3/1996 |
| 2009/0206128 A1 | 8/2009 | Hueil et al. | | EP | 0705571 A1 | 4/1996 |
| 2009/0206129 A1 | 8/2009 | Doll et al. | | EP | 0484677 B2 | 6/1996 |
| 2009/0206130 A1 | 8/2009 | Hall et al. | | EP | 0541987 B1 | 7/1996 |
| 2009/0206131 A1 | 8/2009 | Weisenburgh, II et al. | | EP | 0667119 B1 | 7/1996 |
| 2009/0206132 A1 | 8/2009 | Hueil et al. | | EP | 0770355 A1 | 5/1997 |
| 2009/0206133 A1 | 8/2009 | Morgan et al. | | EP | 0503662 B1 | 6/1997 |
| 2009/0206134 A1 | 8/2009 | Swayze et al. | | EP | 0578425 B1 | 9/1997 |
| 2009/0206135 A1 | 8/2009 | Hall et al. | | EP | 0625335 B1 | 11/1997 |
| 2009/0206136 A1 | 8/2009 | Moore et al. | | EP | 0552423 B1 | 1/1998 |
| 2009/0206137 A1 | 8/2009 | Hall et al. | | EP | 0592244 B1 | 1/1998 |
| 2009/0206138 A1 | 8/2009 | Smith et al. | | EP | 0648476 B1 | 1/1998 |
| 2009/0206139 A1 | 8/2009 | Hall et al. | | EP | 0676173 B1 | 9/1998 |
| 2009/0206140 A1 | 8/2009 | Scheib et al. | | EP | 0603472 B1 | 11/1998 |
| 2009/0206141 A1 | 8/2009 | Huitema et al. | | EP | 0605351 B1 | 11/1998 |
| 2009/0206142 A1 | 8/2009 | Huitema et al. | | EP | 0878169 A1 | 11/1998 |
| 2009/0206143 A1 | 8/2009 | Huitema et al. | | EP | 0879742 A1 | 11/1998 |
| 2009/0206144 A1 | 8/2009 | Doll et al. | | EP | 0760230 B1 | 2/1999 |
| 2009/0209946 A1 | 8/2009 | Swayze et al. | | EP | 0537572 B1 | 6/1999 |
| 2009/0218384 A1 | 9/2009 | Aranyi | | EP | 0552050 B1 | 5/2000 |
| 2009/0242610 A1 | 10/2009 | Shelton, IV et al. | | EP | 1090592 A1 | 4/2001 |
| 2009/0255974 A1 | 10/2009 | Viola | | EP | 1256318 B1 | 5/2001 |
| 2009/0255978 A1 | 10/2009 | Viola et al. | | EP | 0908152 B1 | 1/2002 |
| 2009/0289096 A1 | 11/2009 | Shelton, IV et al. | | EP | 0872213 B1 | 5/2002 |
| 2009/0292283 A1 | 11/2009 | Odom | | EP | 1238634 A2 | 9/2002 |
| 2010/0032470 A1 | 2/2010 | Hess et al. | | EP | 0656188 B1 | 1/2003 |
| 2010/0065605 A1 | 3/2010 | Shelton, VI et al. | | EP | 0829235 B1 | 6/2003 |
| 2010/0065609 A1 | 3/2010 | Schwemberger | | EP | 0813843 B1 | 10/2003 |
| 2010/0069942 A1 | 3/2010 | Shelton, IV | | EP | 0741996 B1 | 2/2004 |
| 2010/0072251 A1 | 3/2010 | Baxter, III et al. | | EP | 0705570 B1 | 4/2004 |
| 2010/0072252 A1 | 3/2010 | Baxter, III et al. | | EP | 1086713 B1 | 5/2004 |
| 2010/0072253 A1 | 3/2010 | Baxter, III et al. | | EP | 1426012 A1 | 6/2004 |
| 2010/0072256 A1 | 3/2010 | Baxter, III et al. | | EP | 0888749 B1 | 9/2004 |
| 2010/0076474 A1 | 3/2010 | Yates et al. | | EP | 1477119 A1 | 11/2004 |
| 2010/0076475 A1 | 3/2010 | Yates et al. | | EP | 1479345 A1 | 11/2004 |
| 2010/0089970 A1 | 4/2010 | Smith et al. | | EP | 1479347 A1 | 11/2004 |
| 2010/0089974 A1 | 4/2010 | Shelton, IV | | EP | 1479348 A1 | 11/2004 |
| 2010/0096435 A1 | 4/2010 | Fuchs et al. | | EP | 1520521 A1 | 4/2005 |
| 2010/0133317 A1 | 6/2010 | Shelton, IV et al. | | EP | 1520523 A1 | 4/2005 |
| 2010/0133318 A1 | 6/2010 | Boudreaux | | EP | 1520525 A1 | 4/2005 |
| 2010/0179382 A1 | 7/2010 | Shelton, IV et al. | | EP | 1522264 A1 | 4/2005 |
| 2010/0181364 A1 | 7/2010 | Shelton, IV et al. | | EP | 1550408 A1 | 7/2005 |
| 2010/0193566 A1 | 8/2010 | Scheib et al. | | EP | 1557129 A1 | 7/2005 |
| 2010/0193567 A1 | 8/2010 | Scheib et al. | | EP | 1064883 B1 | 8/2005 |
| 2010/0193568 A1 | 8/2010 | Scheib et al. | | EP | 1157666 B1 | 9/2005 |
| 2010/0193569 A1 | 8/2010 | Yates et al. | | EP | 1621138 A2 | 2/2006 |
| 2010/0198220 A1 | 8/2010 | Boudreaux et al. | | EP | 1621139 A2 | 2/2006 |
| 2010/0213241 A1 | 8/2010 | Bedi et al. | | EP | 1621141 A2 | 2/2006 |
| | | | | EP | 1621145 A2 | 2/2006 |
| FOREIGN PATENT DOCUMENTS | | | | EP | 1621151 A2 | 2/2006 |
| CA | 2512960 A1 | 1/2006 | | EP | 1652481 A2 | 5/2006 |
| CA | 2514274 A1 | 1/2006 | | EP | 1382303 B1 | 6/2006 |
| DE | 273689 C | 5/1914 | | EP | 1045672 B1 | 8/2006 |
| DE | 1775926 A | 1/1972 | | EP | 1617768 B1 | 8/2006 |
| DE | 9412228 U | 9/1994 | | EP | 1702567 A2 | 9/2006 |
| DE | 19924311 A1 | 11/2000 | | EP | 1129665 B1 | 11/2006 |
| DE | 69328576 T2 | 1/2001 | | EP | 1256317 B1 | 12/2006 |
| DE | 20112837 U1 | 10/2001 | | EP | 1728473 A1 | 12/2006 |
| DE | 20121753 U1 | 4/2003 | | EP | 1728475 A2 | 12/2006 |
| DE | 10314072 A1 | 10/2004 | | EP | 1479346 B1 | 1/2007 |
| EP | 0122046 A1 | 10/1984 | | EP | 1484024 B1 | 1/2007 |

| | | | | | | |
|---|---|---|---|---|---|---|
| EP | 1754445 A2 | 2/2007 | | WO | WO 02/058568 A1 | 8/2002 |
| EP | 1759812 A1 | 3/2007 | | WO | WO 02/060328 A1 | 8/2002 |
| EP | 1769756 A1 | 4/2007 | | WO | WO 02/067785 A2 | 9/2002 |
| EP | 1769758 A1 | 4/2007 | | WO | WO 02/098302 A1 | 12/2002 |
| EP | 1785097 A2 | 5/2007 | | WO | WO 03/000138 A2 | 1/2003 |
| EP | 1790293 A2 | 5/2007 | | WO | WO 03/001329 A2 | 1/2003 |
| EP | 1800610 A1 | 6/2007 | | WO | WO 03/013363 A1 | 2/2003 |
| EP | 1300117 B1 | 8/2007 | | WO | WO 03/020106 A2 | 3/2003 |
| EP | 1813199 A1 | 8/2007 | | WO | WO 03/020139 A2 | 3/2003 |
| EP | 1813201 A1 | 8/2007 | | WO | WO 03/079909 A3 | 3/2003 |
| EP | 1813203 A2 | 8/2007 | | WO | WO 03/030743 A2 | 4/2003 |
| EP | 1813207 A1 | 8/2007 | | WO | WO 03/037193 A1 | 5/2003 |
| EP | 1813209 A1 | 8/2007 | | WO | WO 03/047436 A3 | 6/2003 |
| EP | 1402821 B1 | 12/2007 | | WO | WO 03/057048 A1 | 7/2003 |
| EP | 1872727 A1 | 1/2008 | | WO | WO 03/057058 A1 | 7/2003 |
| EP | 1839596 A2 | 2/2008 | | WO | WO 03/063694 A1 | 8/2003 |
| EP | 1897502 A1 | 3/2008 | | WO | WO 03/077769 A1 | 9/2003 |
| EP | 1702568 B1 | 7/2008 | | WO | WO 03/082126 A1 | 10/2003 |
| EP | 1970014 A1 | 9/2008 | | WO | WO 03/088845 A2 | 10/2003 |
| EP | 1980213 A2 | 10/2008 | | WO | WO 03/090630 A2 | 11/2003 |
| EP | 1759645 B1 | 11/2008 | | WO | WO 03/094743 A1 | 11/2003 |
| EP | 1693008 B1 | 12/2008 | | WO | WO 03/094745 A1 | 11/2003 |
| EP | 2000102 A2 | 12/2008 | | WO | WO 03/094746 A1 | 11/2003 |
| EP | 1749486 B1 | 3/2009 | | WO | WO 03/094747 A1 | 11/2003 |
| EP | 2090256 A2 | 8/2009 | | WO | WO 03/101313 A1 | 12/2003 |
| EP | 1813206 B1 | 4/2010 | | WO | WO 03/105698 A2 | 12/2003 |
| FR | 999646 A | 2/1952 | | WO | WO 03/105702 A2 | 12/2003 |
| FR | 1112936 A | 3/1956 | | WO | WO 2004/006980 A2 | 1/2004 |
| FR | 2765794 A | 1/1999 | | WO | WO 2004/028585 A2 | 4/2004 |
| GB | 939929 A | 10/1963 | | WO | WO 2004/032754 A2 | 4/2004 |
| GB | 1210522 A | 10/1970 | | WO | WO 2004/032760 A2 | 4/2004 |
| GB | 2336214 A | 10/1999 | | WO | WO 2004/032762 A1 | 4/2004 |
| JP | 6007357 A | 1/1994 | | WO | WO 2004/032763 A2 | 4/2004 |
| JP | 7051273 A | 2/1995 | | WO | WO 2004/047653 A2 | 6/2004 |
| JP | 8033641 A | 2/1996 | | WO | WO 2004/049956 A2 | 6/2004 |
| JP | 8229050 A | 9/1996 | | WO | WO 2004/086987 A1 | 10/2004 |
| JP | 2000287987 A | 10/2000 | | WO | WO 2004/096057 A2 | 11/2004 |
| JP | 2001286477 A | 10/2001 | | WO | WO 2004/105621 A1 | 12/2004 |
| JP | 2002369820 A | 12/2002 | | WO | WO 2004/112618 A2 | 12/2004 |
| JP | 2005505322 T | 2/2005 | | WO | WO 2004/112652 A2 | 12/2004 |
| JP | 2005103293 A | 4/2005 | | WO | WO 2005/027983 A2 | 3/2005 |
| RU | 2187249 C2 | 8/2002 | | WO | WO 2005/037329 A2 | 4/2005 |
| RU | 2225170 C2 | 3/2004 | | WO | WO 2005078892 A1 * | 8/2005 |
| SU | 1377053 A1 | 2/1988 | | WO | WO 2005/096954 A2 | 10/2005 |
| SU | 1561964 A1 | 5/1990 | | WO | WO 2005/112808 A1 | 12/2005 |
| SU | 1722476 A1 | 3/1992 | | WO | WO 2005/115251 A2 | 12/2005 |
| WO | WO 93/08755 A1 | 5/1993 | | WO | WO 2006/044490 A2 | 4/2006 |
| WO | WO 95/18572 A1 | 7/1995 | | WO | WO 2006/044581 A2 | 4/2006 |
| WO | WO 95/23557 A1 | 9/1995 | | WO | WO 2006/044810 A2 | 4/2006 |
| WO | WO 95/29639 A1 | 11/1995 | | WO | WO 2006/083748 A1 | 8/2006 |
| WO | WO 96/22055 A1 | 7/1996 | | WO | WO 2006/115958 A1 | 11/2006 |
| WO | WO 96/35464 A1 | 11/1996 | | WO | WO 2006/132992 A1 | 12/2006 |
| WO | WO 97/34533 A1 | 9/1997 | | WO | WO 2007/002180 A2 | 1/2007 |
| WO | WO 97/39688 A2 | 10/1997 | | WO | WO 2007/016290 A2 | 2/2007 |
| WO | WO 98/17180 A1 | 4/1998 | | WO | WO 2007/018898 A2 | 2/2007 |
| WO | WO 98/30153 A1 | 7/1998 | | WO | WO 2007/098220 A2 | 8/2007 |
| WO | WO 99/12483 A1 | 3/1999 | | WO | WO 2007/121579 A1 | 11/2007 |
| WO | WO 99/15086 A1 | 4/1999 | | WO | WO 2007/137304 A2 | 11/2007 |
| WO | WO 99/34744 A1 | 7/1999 | | WO | WO 2007/139734 A2 | 12/2007 |
| WO | WO 99/45849 A1 | 9/1999 | | WO | WO 2007/142625 A2 | 12/2007 |
| WO | WO 00/24322 A1 | 5/2000 | | WO | WO 2008/039270 A1 | 4/2008 |
| WO | WO 00/57796 A1 | 10/2000 | | WO | WO 2008/045383 A2 | 4/2008 |
| WO | WO 00/64365 A1 | 11/2000 | | | | |
| WO | WO 00/72762 A1 | 12/2000 | | | | |
| WO | WO 00/72765 A1 | 12/2000 | | | | |
| WO | WO 01/05702 A1 | 1/2001 | | | | |
| WO | WO 01/10482 A1 | 2/2001 | | | | |
| WO | WO 01/54594 A1 | 8/2001 | | | | |
| WO | WO 01/62158 A2 | 8/2001 | | | | |
| WO | WO 01/62162 A1 | 8/2001 | | | | |
| WO | WO 01/62164 A2 | 8/2001 | | | | |
| WO | WO 01/91646 A1 | 12/2001 | | | | |
| WO | WO 02/07608 A2 | 1/2002 | | | | |
| WO | WO 02/07618 A1 | 1/2002 | | | | |
| WO | WO 02/17799 A1 | 3/2002 | | | | |
| WO | WO 02/19920 A1 | 3/2002 | | | | |
| WO | WO 02/30297 A2 | 4/2002 | | | | |
| WO | WO 02/32322 A2 | 4/2002 | | | | |
| WO | WO 02/43571 A2 | 6/2002 | | | | |

OTHER PUBLICATIONS

European Examination Report, Application No. 08250099.2, dated Mar. 17, 2009 (4 pages).

Disclosed Anonymously, "Motor-Driven Surgical Stapler Improvements," Research Disclosure Database No. 526041, Published: Feb. 2008.

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.

7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

The Sodem Aseptic Battery Transfer Kit, Sodem Systems, 2000, 3 pages.

"Biomedical Coatings," Fort Wayne Metals, Research Products Corporation, obtained online at www.fwmetals.com on Jun. 21, 2010 (1 page).

* cited by examiner

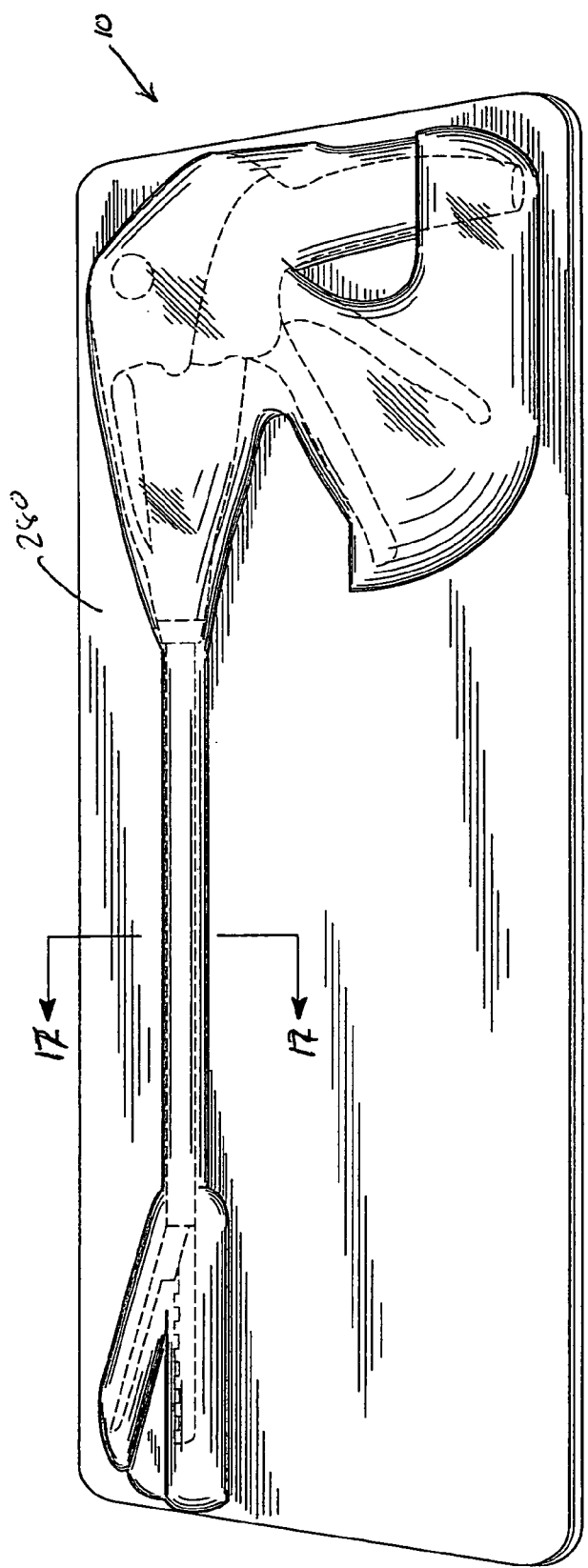
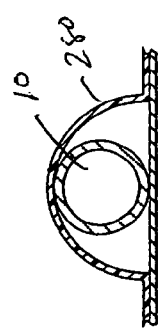
FIG. 14
FIG. 15

SURGICAL INSTRUMENT WITH ENHANCED BATTERY PERFORMANCE

CROSS-REFERENCE TO RELATED APPLICATIONS

The present application is related to the following, concurrently-filed U.S. patent applications, which are incorporated herein by reference:

(1) U.S. patent application Ser. No. 11/651,715, now U.S. Patent Publication No. 2008/0167522, entitled "SURGICAL INSTRUMENT WITH WIRELESS COMMUNICATION BETWEEN CONTROL UNIT AND SENSOR TRANSPONDERS," by J. Giordano et al.;

(2) U.S. patent application Ser. No. 11/651,807, now U.S. Patent Publication No. 2008/0167672, entitled "SURGICAL INSTRUMENT WITH WIRELESS COMMUNICATION BETWEEN CONTROL UNIT AND REMOTE SENSOR," by J. Giordano et al.;

(3) U.S. patent application Ser. No. 11/651,806, now U.S. Patent Publication No. 2008/0167671, entitled "SURGICAL INSTRUMENT WITH ELEMENTS TO COMMUNICATE BETWEEN CONTROL UNIT AND END EFFECTOR," by J. Giordano et al.;

(4) U.S. patent application Ser. No. 11/651,768, now U.S. Pat. No. 7,721,931, entitled "PREVENTION OF CARTRIDGE REUSE IN A SURGICAL INSTRUMENT," by F. Shelton et al.;

(5) U.S. patent application Ser. No. 11/651,771, now U.S. Pat. No. 7,738,971, entitled "POST-STERILIZATION PROGRAMMING OF SURGICAL INSTRUMENTS," by J. Swayze et al.; and (6) U.S. patent application Ser. No. 11/651,788, now U.S. Pat. No. 7,721,936, entitled "INTERLOCK AND SURGICAL INSTRUMENT INCLUDING SAME, by F. Shelton et al.

BACKGROUND

Endoscopic surgical instruments are often preferred over traditional open surgical devices since a smaller incision tends to reduce the post-operative recovery time and complications. Consequently, significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

Known surgical staplers include an end effector that simultaneously makes a longitudinal incision in tissue and applies lines of staples on opposing sides of the incision. The end effector includes a pair of cooperating jaw members that, if the instrument is intended for endoscopic or laparoscopic applications, are capable of passing through a cannula passageway. One of the jaw members receives a staple cartridge having at least two laterally spaced rows of staples. The other jaw member defines an anvil having staple-forming pockets aligned with the rows of staples in the cartridge. The instrument includes a plurality of reciprocating wedges which, when driven distally, pass through openings in the staple cartridge and engage drivers supporting the staples to effect the firing of the staples toward the anvil.

An example of a surgical stapler suitable for endoscopic applications is described in U.S. Pat. No. 5,465,895, which discloses an endocutter with distinct closing and firing actions. A clinician using this device is able to close the jaw members upon tissue to position the tissue prior to firing. Once the clinician has determined that the jaw members are properly gripping tissue, the clinician can then fire the surgical stapler with a single firing stroke, thereby severing and stapling the tissue. The simultaneous severing and stapling avoids complications that may arise when performing such actions sequentially with different surgical tools that respectively only sever and staple.

One specific advantage of being able to close upon tissue before firing is that the clinician is able to verify via an endoscope that the desired location for the cut has been achieved, including that a sufficient amount of tissue has been captured between opposing jaws. Otherwise, opposing jaws may be drawn too close together, especially pinching at their distal ends, and thus not effectively forming closed staples in the severed tissue. At the other extreme, an excessive amount of clamped tissue may cause binding and an incomplete firing.

Endoscopic staplers/cutters continue to increase in complexity and function with each generation. One reason for this is the quest to lower force-to-fire (FTF) to a level that all or a great majority of surgeons can handle. One known solution to lower FTF uses $CO_2$ or electrical motors. These devices have not faired much better than traditional hand-powered devices, but for a different reason. Surgeons typically prefer to experience proportionate force distribution to that being experienced by the end effector in the forming of the staple to assure them that the cutting/stapling cycle is complete, with the upper limit within the capabilities of most surgeons (usually around 15-30 lbs). They also typically want to maintain control of deploying the staples and being able to stop at anytime if the forces felt in the handle of the device feel too great or for some other clinical reason.

To address this need, so-called "power-assist" endoscopic surgical instruments have been developed in which a supplemental power source aids in the firing of the instrument. For example, in some power-assist devices, a motor provides supplemental electrical power to the power input by the user from squeezing the firing trigger. Such devices are capable of providing loading force feedback and control to the operator to reduce the firing force required to be exerted by the operator in order to complete the cutting operation. One such power-assist device is described in U.S. patent application Ser. No. 11/343,573, filed Jan. 31, 2006 by Shelton et al., entitled "Motor-driven surgical cutting and fastening instrument with loading force feedback," ("the '573 application") which is incorporated herein by reference.

Another reason for the increase in complexity and function of endoscopic surgical instruments is the quest to monitor and provide increased control over instrument components. For example, sensors and control systems are now being used to implement new functionality in surgical instruments including, for example, electronic lock-outs. For example, One such lockout device is described in U.S. patent application Ser. No. 11/343,439, filed Jan. 31, 2006 by Swayze et al., entitled, "Electronic Lockouts And Surgical Instrument Including Same," which is incorporated herein by reference.

One challenge in using electronics in any kind of surgical instrument is providing a suitable power source. Most surgical instruments are stocked in sealed, sterilized packages. Because of this, it is usually not practical to access an instrument after it is packaged to verify the status of its power source or recharge if necessary. Accordingly, the shelf-life of the instrument is limited by the time that the power source is able to reliably hold a charge. For many kinds of instruments, though, it is desirable to choose a power source with a high peak power output. A high peak power output makes a power source more suitable for driving the motors, sensors and control systems used in surgical instruments. Sources with a high peak power output, however, such as lithium ion batteries, typically do not hold a full charge for a suitably long time. Accordingly, the choice of a power source must compromise the need for high peak power with a corresponding need for a long shelf-life.

SUMMARY

In one general aspect, the present invention is directed to an assembly including a component of a surgical instrument, such as an endoscopic or laparoscopic instrument. The assembly may comprise a package; a surgical instrument component within the package; and a power source within the package. The power source may be configured to be placed in electrical communication with the surgical instrument component. The assembly may also comprise an auxiliary power source within the package and a circuit element, where the circuit element is in electrical communication with the power source and the auxiliary power source.

In another general aspect, the present invention is directed to an end effector cartridge for use with a surgical instrument. The end effector cartridge may comprise an electrical component; a power source; and a circuit element. The circuit element may be configured to electrically connect the power source and the electrical component when the end effector cartridge is installed in a surgical instrument.

In yet another general aspect, the present invention is directed to an assembly comprising a package and an end effector cartridge within the package. The end effector cartridge may comprise an electrical component. The assembly may also comprise a power source within the package and a circuit element within the package. The circuit element may be configured to electrically connect the power source and the electrical component when the end effector cartridge is installed in a surgical instrument. Methods of reconditioning surgical instruments and components thereof are also disclosed.

FIGURES

Various embodiments of the present invention are described herein by way of example in conjunction with the following figures wherein:

FIGS. 14-16 show the instrument in a sterile package according to various embodiments of the present invention;

DESCRIPTION

Various embodiments of the present invention are directed generally to surgical instruments and/or instrument components having power sources whose charges can be applied or maintained while the instruments and/or components are sealed in a sterile package. The present invention may be used with any type of surgical instrument comprising at least one power source, such as endoscopic or laparoscopic surgical instruments. Before describing aspects of the system, one type of surgical instrument in which embodiments of the present invention may be used—an endoscopic stapling and cutting instrument (i.e., an endocutter)—is first described by way of illustration.

Figure 1:
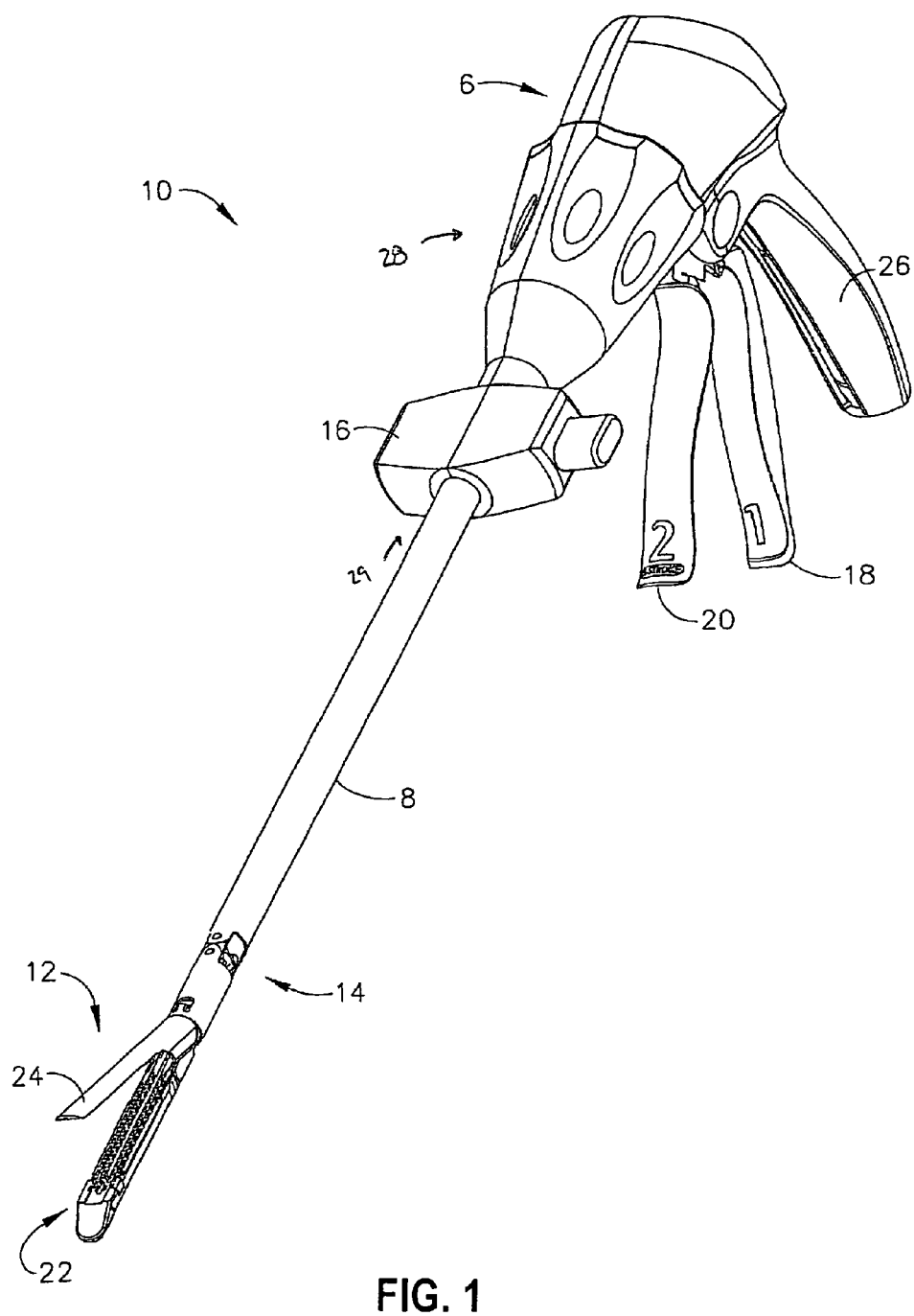
FIGS. 1 and 2 are perspective views of a surgical instrument according to various embodiments of the present invention.
Figure 2:
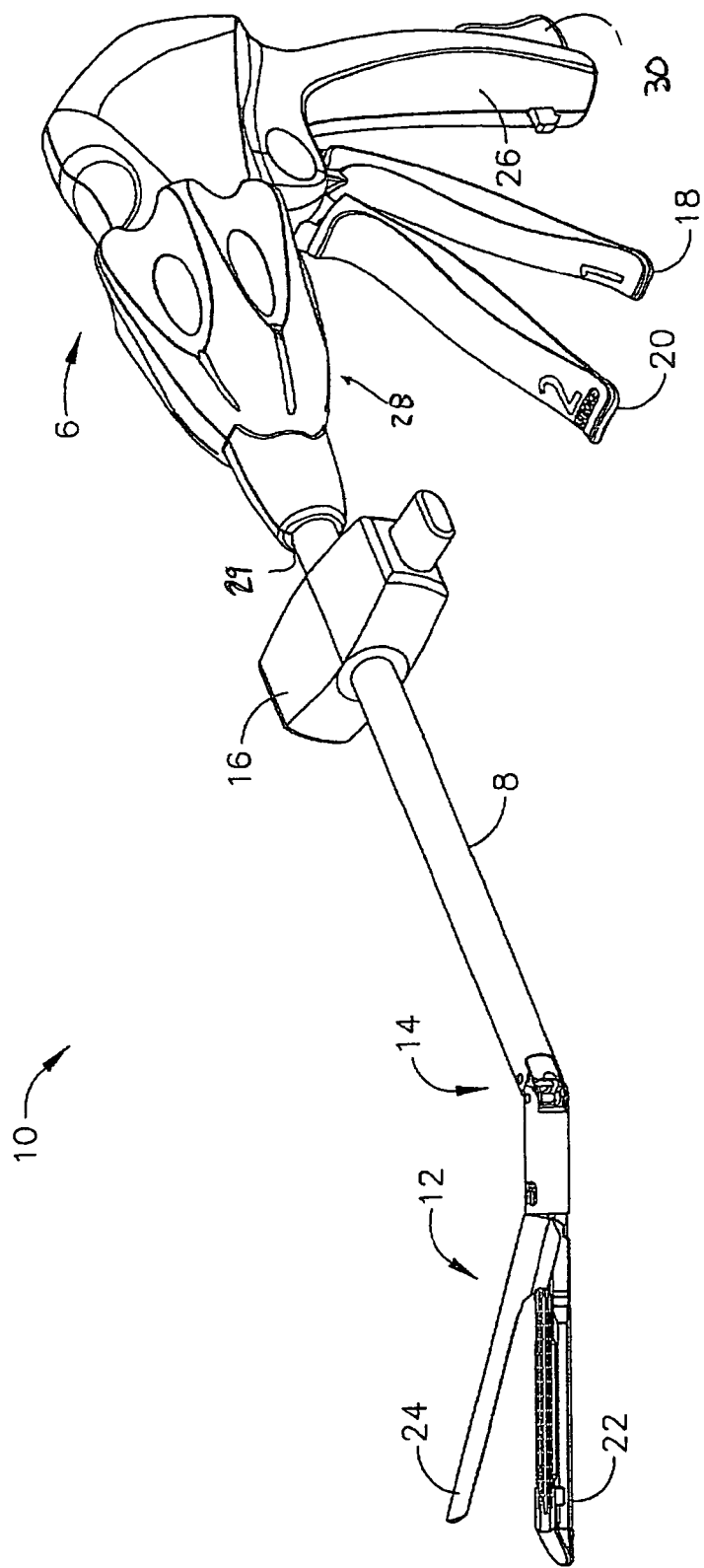

FIGS. 1 and 2 depict an endoscopic surgical instrument 10 that comprises a handle 6, a shaft 8, and an articulating end effector 12 pivotally connected to the shaft 8 at an articulation pivot 14. Correct placement and orientation of the end effector 12 may be facilitated by controls on the hand 6, including (1) a rotation knob 28 for rotating the closure tube (described in more detail below in connection with FIGS. 4-5) at a free rotating joint 29 of the shaft 8 to thereby rotate the end effector 12 and (2) an articulation control 16 to effect rotational articulation of the end effector 12 about the articulation pivot 14. In the illustrated embodiment, the end effector 12 is configured to act as an endocutter for clamping, severing and stapling tissue, although in other embodiments, different types of end effectors may be used, such as end effectors for other types of surgical instruments, such as graspers, cutters, staplers, clip appliers, access devices, drug/gene therapy devices, ultrasound, RF or laser devices, etc.

The handle 6 of the instrument 10 may include a closure trigger 18 and a firing trigger 20 for actuating the end effector 12. It will be appreciated that instruments having end effectors directed to different surgical tasks may have different numbers or types of triggers or other suitable controls for operating the end effector 12. The end effector 12 is shown separated from the handle 6 by the preferably elongate shaft 8. In one embodiment, a clinician or operator of the instrument 10 may articulate the end effector 12 relative to the shaft 8 by utilizing the articulation control 16, as described in more detail in pending U.S. patent application Ser. No. 11/329,020, filed Jan. 10, 2006, entitled "Surgical Instrument Having An Articulating End Effector," by Geoffrey C. Hueil et al., which is incorporated herein by reference.

In this example, the end effector 12 includes, among other things, a staple channel 22 and a pivotally translatable clamping member, such as an anvil 24, which are maintained at a spacing that assures effective stapling and severing of tissue clamped in the end effector 12. The handle 6 includes a pistol grip 26 towards which a closure trigger 18 is pivotally drawn by the clinician to cause clamping or closing of the anvil 24 toward the staple channel 22 of the end effector 12 to thereby clamp tissue positioned between the anvil 24 and channel 22. The firing trigger 20 is farther outboard of the closure trigger 18. Once the closure trigger 18 is locked in the closure position, the firing trigger 20 may rotate slightly toward the pistol grip 26 so that it can be reached by the operator using one hand. Then the operator may pivotally draw the firing trigger 20 toward the pistol grip 12 to cause the stapling and severing of clamped tissue in the end effector 12. The '573 application describes various configurations for locking and unlocking the closure trigger 18. In other embodiments, different types of clamping members besides the anvil 24 could be used, such as, for example, an opposing jaw, etc.

It will be appreciated that the terms "proximal" and "distal" are used herein with reference to a clinician gripping the handle 6 of an instrument 10. Thus, the end effector 12 is distal with respect to the more proximal handle 6. It will be further appreciated that, for convenience and clarity, spatial terms such as "vertical" and "horizontal" are used herein with respect to the drawings. However, surgical instruments are used in many orientations and positions, and these terms are not intended to be limiting and absolute.

The closure trigger 18 may be actuated first. Once the clinician is satisfied with the positioning of the end effector 12, the clinician may draw back the closure trigger 18 to its fully closed, locked position proximate to the pistol grip 26. The firing trigger 20 may then be actuated. The firing trigger 20 returns to the open position (shown in FIGS. 1 and 2) when the clinician removes pressure. A release button 30 on the handle 6, and in this example, on the pistol grip 26 of the handle, when depressed may release the locked closure trigger 18.

Figure 3:
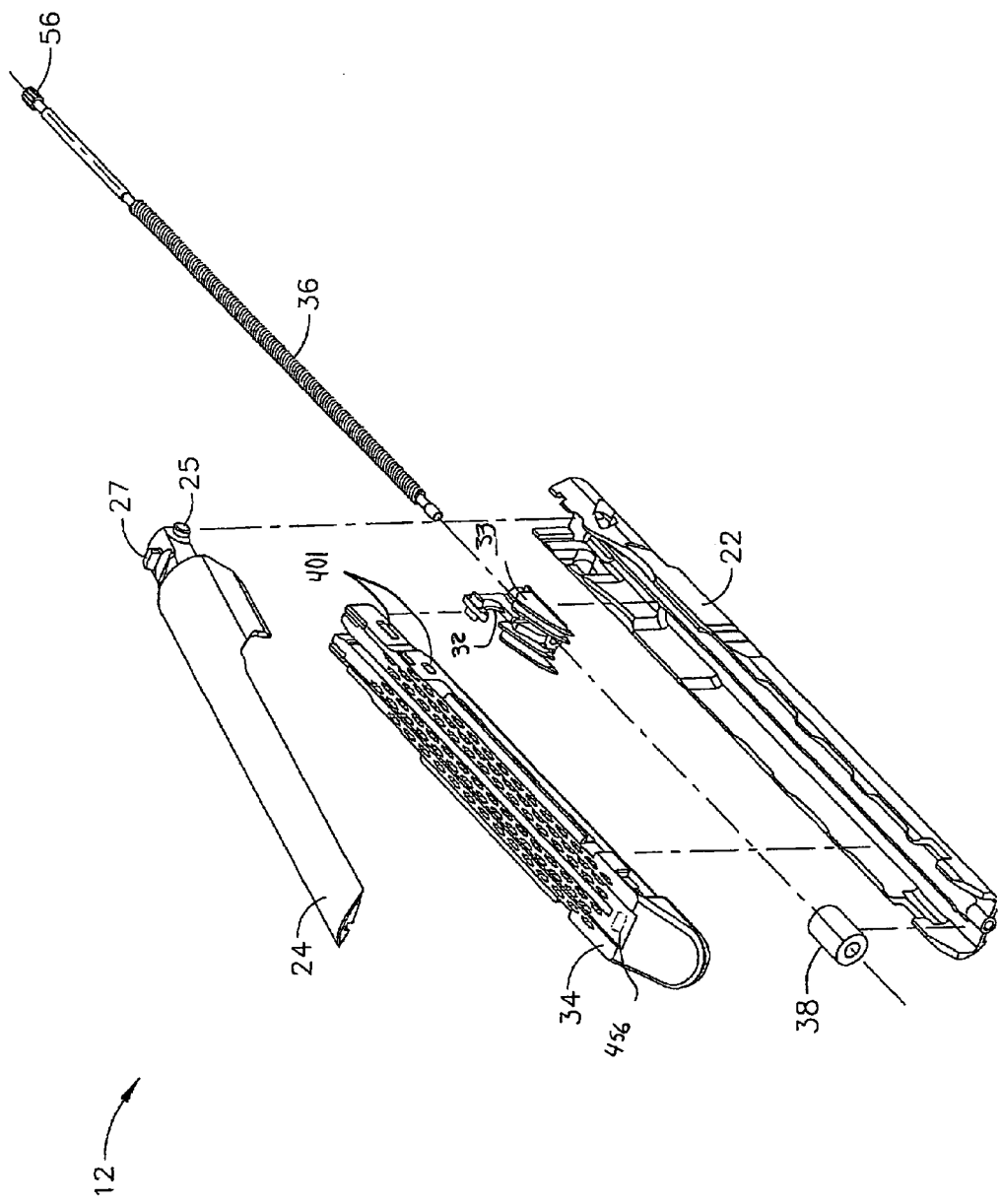
FIGS. 3-5 are exploded views of an end effector and shaft of the instrument according to various embodiments of the present invention.

FIG. 3 is an exploded view of the end effector 12 according to various embodiments. As shown in the illustrated embodiment, the end effector 12 may include, in addition to the previously-mentioned channel 22 and anvil 24, a cutting instrument 32, a sled 33, a staple cartridge 34 that is removably seated in the channel 22, and a helical screw shaft 36. The cutting instrument 32 may be, for example, a knife. The anvil 24 may be pivotably opened and closed at a pivot point 25 connected to the proximate end of the channel 22. The anvil 24 may also include a tab 27 at its proximate end that is inserted into a component of the mechanical closure system (described further below) to open and close the anvil 24. When the closure trigger 18 is actuated, that is, drawn in by a user of the instrument 10, the anvil 24 may pivot about the pivot point 25 into the clamped or closed position. If clamping of the end effector 12 is satisfactory, the operator may actuate the firing trigger 20, which, as explained in more detail below, causes the knife 32 and sled 33 to travel longitudinally along the channel 22, thereby cutting tissue clamped within the end effector 12. The movement of the sled 33 along the channel 22 causes the staples of the staple cartridge 34 to be driven through the severed tissue and against the closed anvil 24, which turns the staples to fasten the severed tissue. U.S. Pat. No. 6,978,921, entitled "Surgical stapling instrument incorporating an E-beam firing mechanism," which is incorporated herein by reference, provides more details about such two-stroke cutting and fastening instruments. The sled 33 may be part of the cartridge 34, such that when the knife 32 retracts following the cutting operation, the sled 33 does not retract. The channel 22 and the anvil 24 may be made of an electrically conductive material (such as metal) and in various embodiments may serve as part of an antenna for communication with sensor(s) in the end effector. The cartridge 34 could be made of a nonconductive material (such as plastic) and the sensor may be connected to or disposed in the cartridge 34, as described further below.

It should be noted that, although the embodiments of the instrument 10 described herein employ an end effector 12 that staples the severed tissue, in other embodiments different techniques for fastening or sealing the severed tissue may be used. For example, end effectors that use RF energy or adhesives to fasten the severed tissue may also be used. U.S. Pat. No. 5,709,680, entitled "Electrosurgical Hemostatic Device" to Yates et al., and U.S. Pat. No. 5,688,270, entitled "Electrosurgical Hemostatic Device With Recessed And/Or Offset Electrodes" to Yates et al., which are incorporated herein by reference, disclose cutting instruments that use RF energy to fasten the severed tissue. U.S. patent application Ser. No. 11/267,811 to Morgan et al and U.S. patent application Ser. No. 11/267,363 to Shelton et al., which are also incorporated herein by reference, disclose cutting instruments that use adhesives to fasten the severed tissue. Accordingly, although the description herein refers to cutting/stapling operations and the like, it should be recognized that this is an exemplary embodiment and is not meant to be limiting. Other tissue-fastening techniques may also be used.

Figure 4:
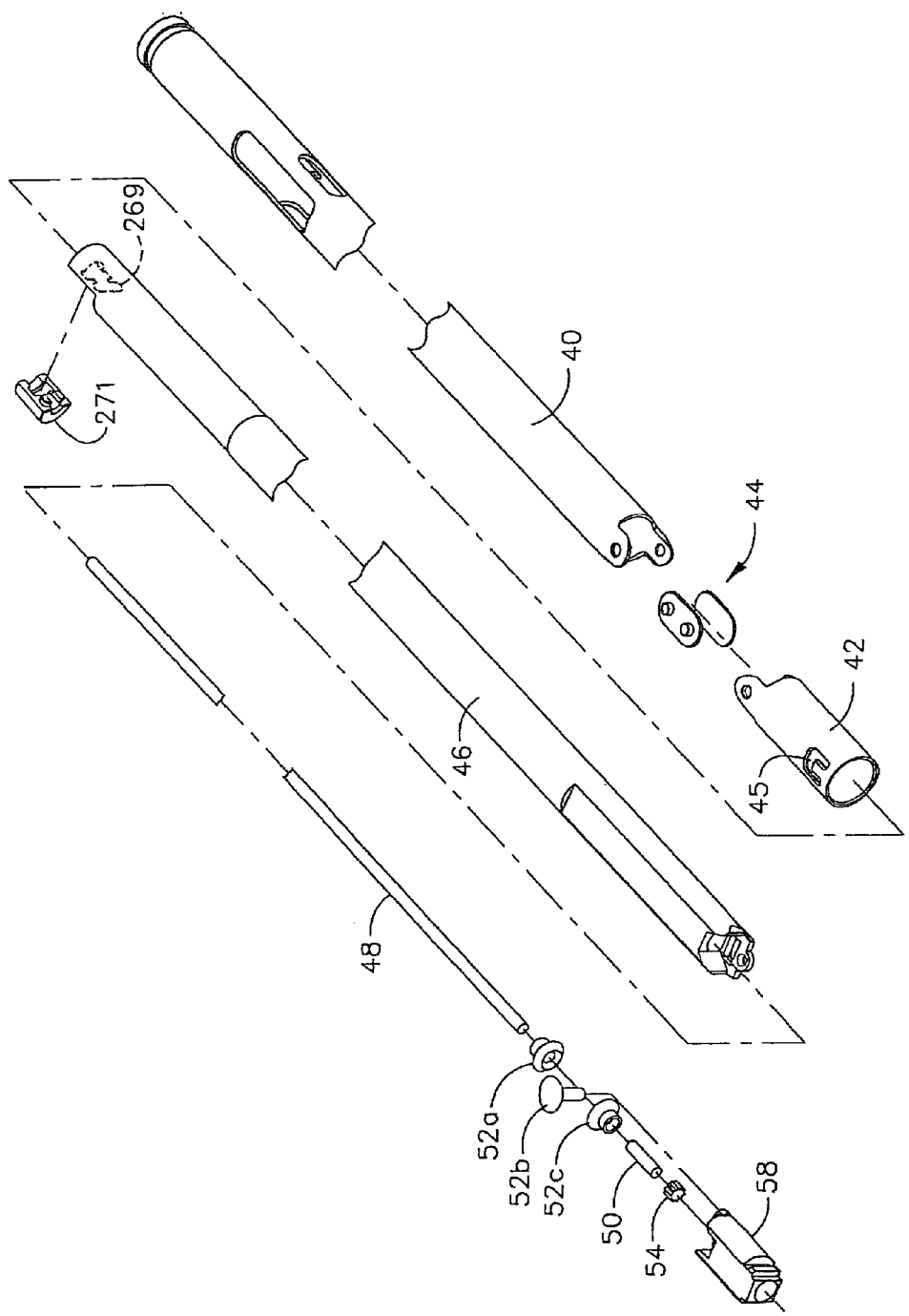
Figure 5:
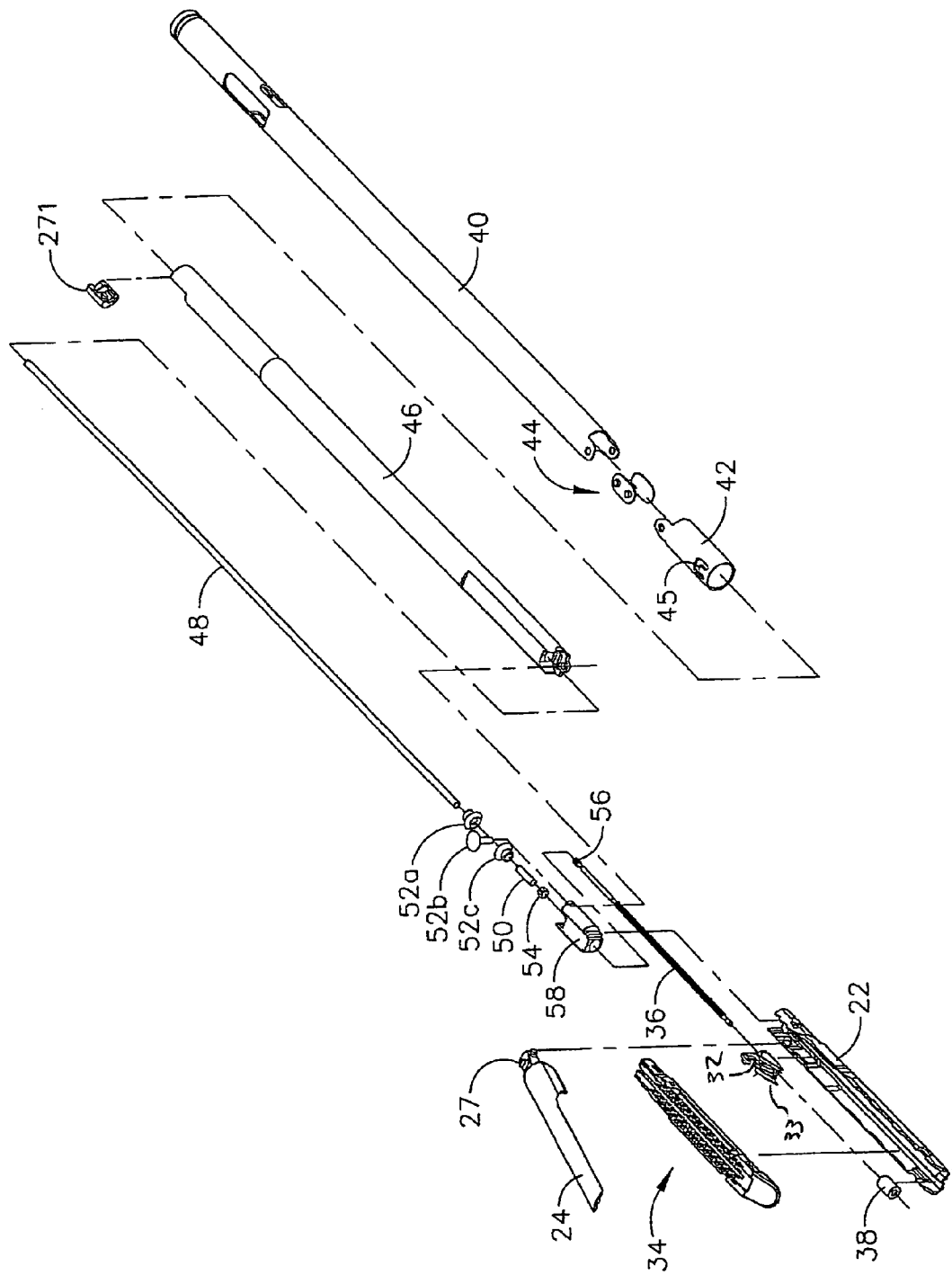
Figure 6:
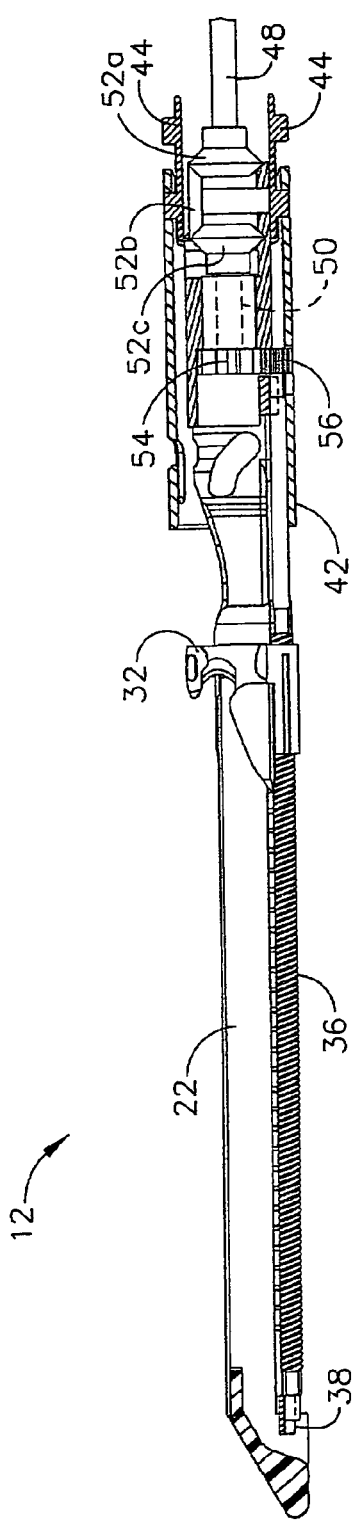
FIG. 6 is a side view of the end effector according to various embodiments of the present invention.
Figure 7:
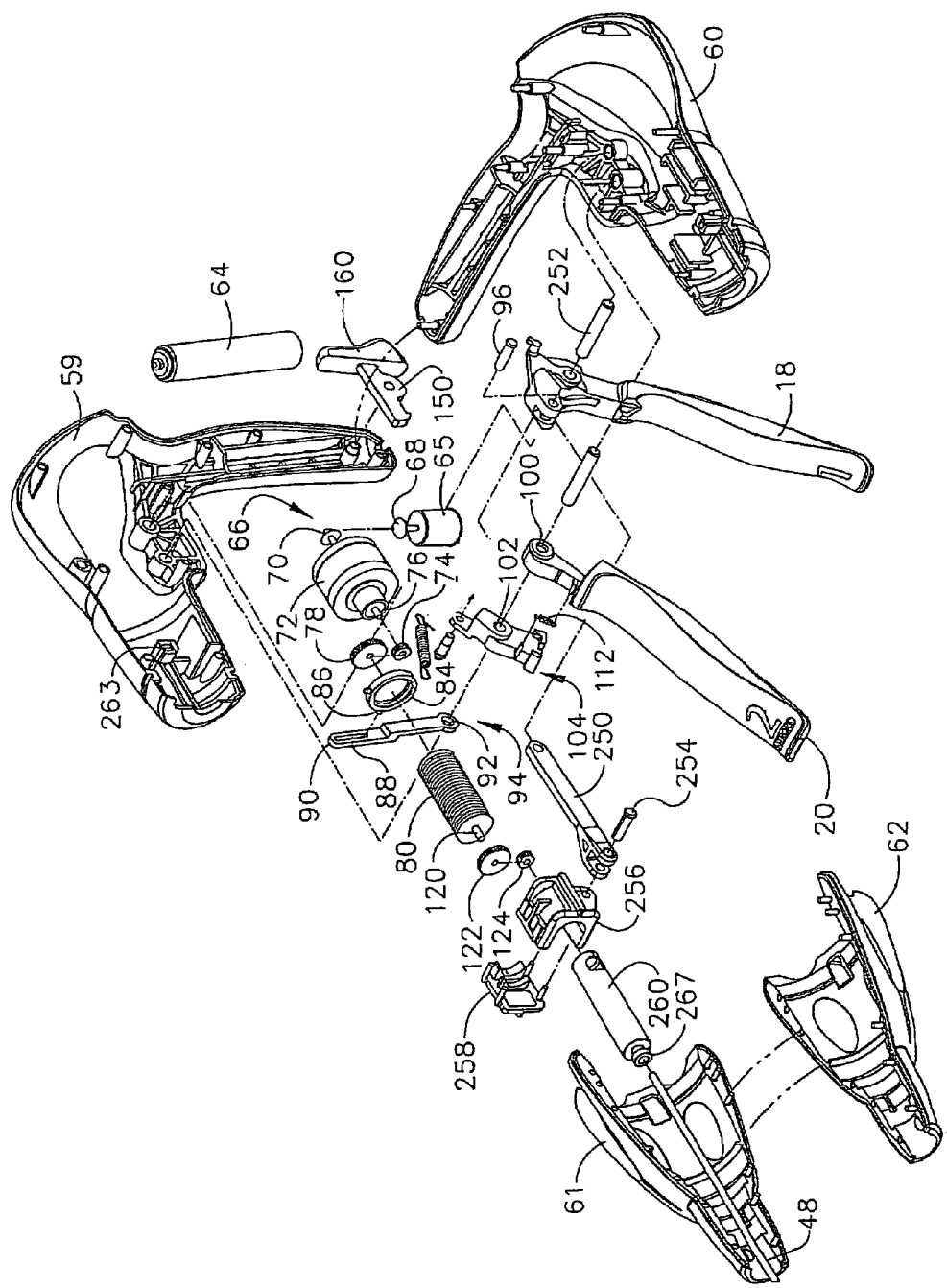
FIG. 7 is an exploded view of the handle of the instrument according to various embodiments of the present invention.

FIGS. 4 and 5 are exploded views and FIG. 6 is a side view of the end effector 12 and shaft 8 according to various embodiments. As shown in the illustrated embodiment, the shaft 8 may include a proximate closure tube 40 and a distal closure tube 42 pivotably linked by a pivot links 44. The distal closure tube 42 includes an opening 45 into which the tab 27 on the anvil 24 is inserted in order to open and close the anvil 24. Disposed inside the closure tubes 40, 42 may be a proximate spine tube 46. Disposed inside the proximate spine tube 46 may be a main rotational (or proximate) drive shaft 48 that communicates with a secondary (or distal) drive shaft 50 via a bevel gear assembly 52. The secondary drive shaft 50 is connected to a drive gear 54 that engages a proximate drive gear 56 of the helical screw shaft 36. The vertical bevel gear 52b may sit and pivot in an opening 57 in the distal end of the proximate spine tube 46. A distal spine tube 58 may be used to enclose the secondary drive shaft 50 and the drive gears 54, 56. Collectively, the main drive shaft 48, the secondary drive shaft 50, and the articulation assembly (e.g., the bevel gear assembly 52a-c), are sometimes referred to herein as the "main drive shaft assembly."

A bearing 38, positioned at a distal end of the staple channel 22, receives the helical drive screw 36, allowing the helical drive screw 36 to freely rotate with respect to the channel 22. The helical screw shaft 36 may interface a threaded opening (not shown) of the knife 32 such that rotation of the shaft 36 causes the knife 32 to translate distally or proximately (depending on the direction of the rotation) through the staple channel 22. Accordingly, when the main drive shaft 48 is caused to rotate by actuation of the firing trigger 20 (as explained in more detail below), the bevel gear assembly 52a-c causes the secondary drive shaft 50 to rotate, which in turn, because of the engagement of the drive gears 54, 56, causes the helical screw shaft 36 to rotate, which causes the knife 32 to travel longitudinally along the channel 22 to cut any tissue clamped within the end effector. The sled 33 may be made of, for example, plastic, and may have a sloped distal surface. As the sled 33 traverses the channel 22, the sloped forward surface may push up or drive the staples in the staple cartridge 34 through the clamped tissue and against the anvil 24. The anvil 24 turns the staples, thereby stapling the severed tissue. When the knife 32 is retracted, the knife 32 and sled 33 may become disengaged, thereby leaving the sled 33 at the distal end of the channel 22.

According to various embodiments, as shown FIGS. 7-10, the surgical instrument may include a battery 64 in the handle 6. The illustrated embodiment provides user-feedback regarding the deployment and loading force of the cutting instrument in the end effector 12. In addition, the embodiment may use power provided by the user in retracting the firing trigger 18 to power the instrument 10 (a so-called "power assist" mode). As shown in the illustrated embodiment, the handle 6 includes exterior lower side pieces 59, 60 and exterior upper side pieces 61, 62 that fit together to form, in general, the exterior of the handle 6. The handle pieces 59-62 may be made of an electrically nonconductive material, such as plastic. A battery 64, such as a lithium ion battery, may be provided in the pistol grip portion 26 of the handle 6. The battery 64 powers a motor 65 disposed in an upper portion of the pistol grip portion 26 of the handle 6. The battery 64 may be constructed according to any suitable construction or chemistry including, for example, a Li-ion chemistry such as $LiCoO_2$ or $LiNiO_2$, a Nickel Metal Hydride chemistry, etc. According to various embodiments, the motor 65 may be a DC brushed driving motor having a maximum rotation of, approximately, 5000 RPM to 100,000 RPM. The motor 64 may drive a 90° bevel gear assembly 66 comprising a first bevel gear 68 and a second bevel gear 70. The bevel gear assembly 66 may drive a planetary gear assembly 72. The planetary gear assembly 72 may include a pinion gear 74 connected to a drive shaft 76. The pinion gear 74 may drive a mating ring gear 78 that drives a helical gear drum 80 via a drive shaft 82. A ring 84 may be threaded on the helical gear drum 80. Thus, when the motor 65 rotates, the ring 84 is caused to travel along the helical gear drum 80 by means of the interposed bevel gear assembly 66, planetary gear assembly 72 and ring gear 78.

The handle 6 may also include a run motor sensor 110 in communication with the firing trigger 20 to detect when the firing trigger 20 has been drawn in (or "closed") toward the pistol grip portion 26 of the handle 6 by the operator to thereby actuate the cutting/stapling operation by the end effector 12. The sensor 110 may be a proportional sensor such as, for example, a rheostat or variable resistor. When the firing trigger 20 is drawn in, the sensor 110 detects the movement, and sends an electrical signal indicative of the voltage (or power) to be supplied to the motor 65. When the sensor 110 is a variable resistor or the like, the rotation of the motor 65 may be generally proportional to the amount of movement of the firing trigger 20. That is, if the operator only draws or closes the firing trigger 20 in a little bit, the rotation of the motor 65 is relatively low. When the firing trigger 20 is fully drawn in (or in the fully closed position), the rotation of the motor 65 is at its maximum. In other words, the harder the user pulls on the firing trigger 20, the more voltage is applied to the motor 65, causing greater rates of rotation. In another embodiment, for example, the control unit (described further below) may output a PWM control signal to the motor 65 based on the input from the sensor 110 in order to control the motor 65.

The handle 6 may include a middle handle piece 104 adjacent to the upper portion of the firing trigger 20. The handle 6 also may comprise a bias spring 112 connected between posts on the middle handle piece 104 and the firing trigger 20. The bias spring 112 may bias the firing trigger 20 to its fully open position. In that way, when the operator releases the firing trigger 20, the bias spring 112 will pull the firing trigger 20 to its open position, thereby removing actuation of the sensor 110, thereby stopping rotation of the motor 65. Moreover, by virtue of the bias spring 112, any time a user closes the firing trigger 20, the user will experience resistance to the closing operation, thereby providing the user with feedback as to the amount of rotation exerted by the motor 65. Further, the operator could stop retracting the firing trigger 20 to thereby remove force from the sensor 100, to thereby stop the motor 65. As such, the user may stop the deployment of the end effector 12, thereby providing a measure of control of the cutting/fastening operation to the operator.

The distal end of the helical gear drum 80 includes a distal drive shaft 120 that drives a ring gear 122, which mates with a pinion gear 124. The pinion gear 124 is connected to the main drive shaft 48 of the main drive shaft assembly. In that way, rotation of the motor 65 causes the main drive shaft assembly to rotate, which causes actuation of the end effector 12, as described above.

The ring 84 threaded on the helical gear drum 80 may include a post 86 that is disposed within a slot 88 of a slotted arm 90. The slotted arm 90 has an opening 92 at its opposite end 94 that receives a pivot pin 96 that is connected between the handle exterior side pieces 59, 60. The pivot pin 96 is also disposed through an opening 100 in the firing trigger 20 and an opening 102 in the middle handle piece 104.

In addition, the handle 6 may include a reverse motor (or end-of-stroke sensor) 130 and a stop motor (or beginning-of-stroke) sensor 142. In various embodiments, the reverse motor sensor 130 may be a limit switch located at the distal end of the helical gear drum 80 such that the ring 84 threaded on the helical gear drum 80 contacts and trips the reverse motor sensor 130 when the ring 84 reaches the distal end of the helical gear drum 80. The reverse motor sensor 130, when activated, sends a signal to the control unit which sends a signal to the motor 65 to reverse its rotation direction, thereby withdrawing the knife 32 of the end effector 12 following the cutting operation.

The stop motor sensor 142 may be, for example, a normally-closed limit switch. In various embodiments, it may be located at the proximate end of the helical gear drum 80 so that the ring 84 trips the switch 142 when the ring 84 reaches the proximate end of the helical gear drum 80.

In operation, when an operator of the instrument 10 pulls back the firing trigger 20, the sensor 110 detects the deployment of the firing trigger 20 and sends a signal to the control unit which sends a signal to the motor 65 to cause forward rotation of the motor 65 at, for example, a rate proportional to how hard the operator pulls back the firing trigger 20. The forward rotation of the motor 65 in turn causes the ring gear 78 at the distal end of the planetary gear assembly 72 to rotate, thereby causing the helical gear drum 80 to rotate, causing the ring 84 threaded on the helical gear drum 80 to travel distally along the helical gear drum 80. The rotation of the helical gear drum 80 also drives the main drive shaft assembly as described above, which in turn causes deployment of the knife 32 in the end effector 12. That is, the knife 32 and sled 33 are caused to traverse the channel 22 longitudinally, thereby cutting tissue clamped in the end effector 12. Also, the stapling operation of the end effector 12 is caused to happen in embodiments where a stapling-type end effector is used.

By the time the cutting/stapling operation of the end effector 12 is complete, the ring 84 on the helical gear drum 80 will have reached the distal end of the helical gear drum 80, thereby causing the reverse motor sensor 130 to be tripped, which sends a signal to the control unit which sends a signal to the motor 65 to cause the motor 65 to reverse its rotation. This in turn causes the knife 32 to retract, and also causes the ring 84 on the helical gear drum 80 to move back to the proximate end of the helical gear drum 80.

Figure 8:
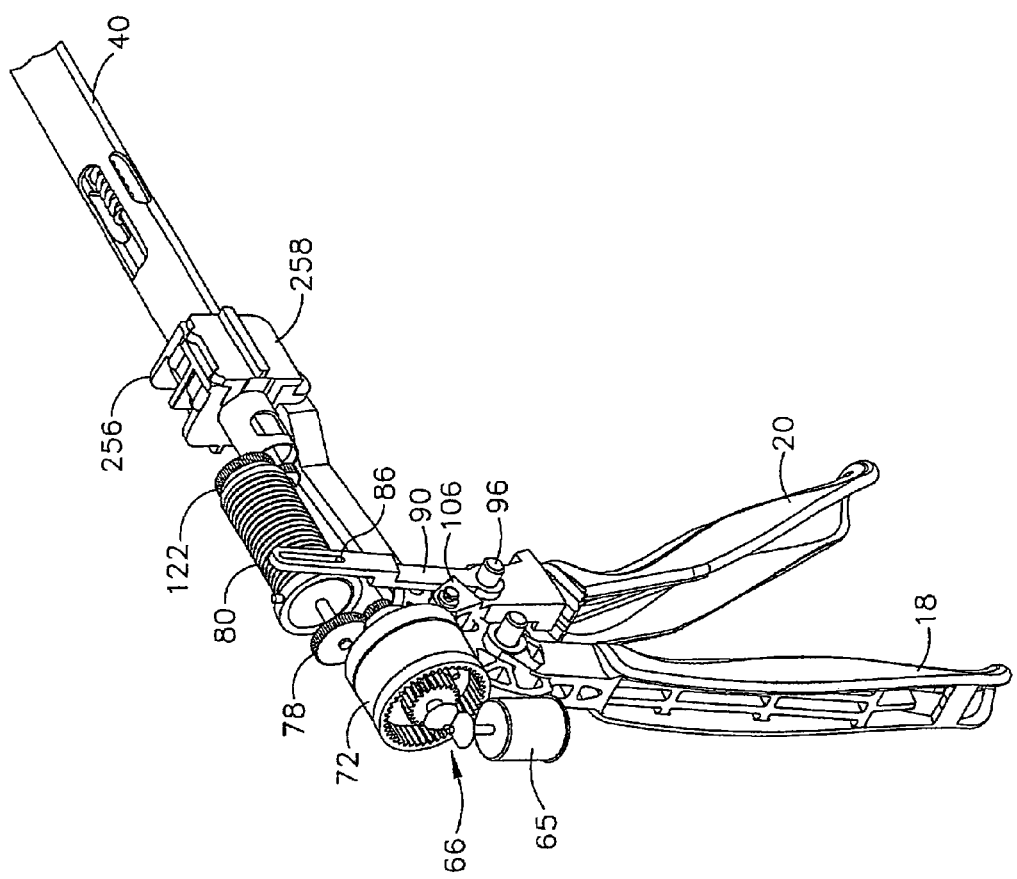
FIGS. 8 and 9 are partial perspective views of the handle according to various embodiments of the present invention.
Figure 9:
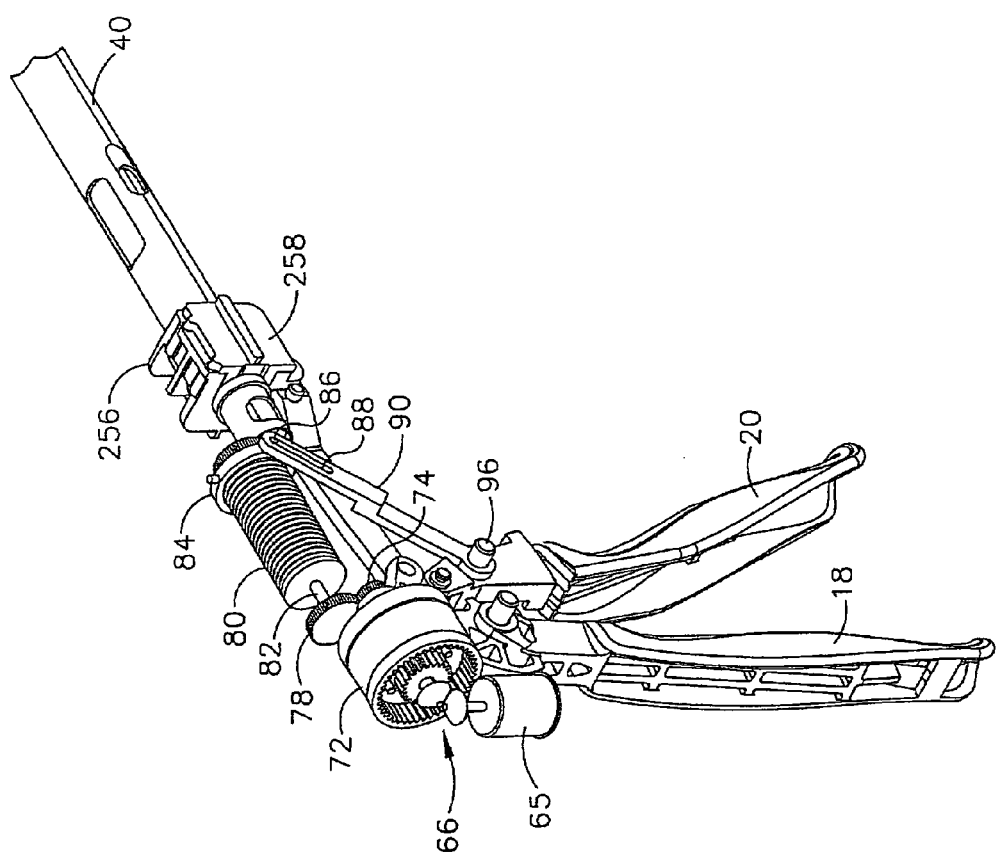
Figure 10:
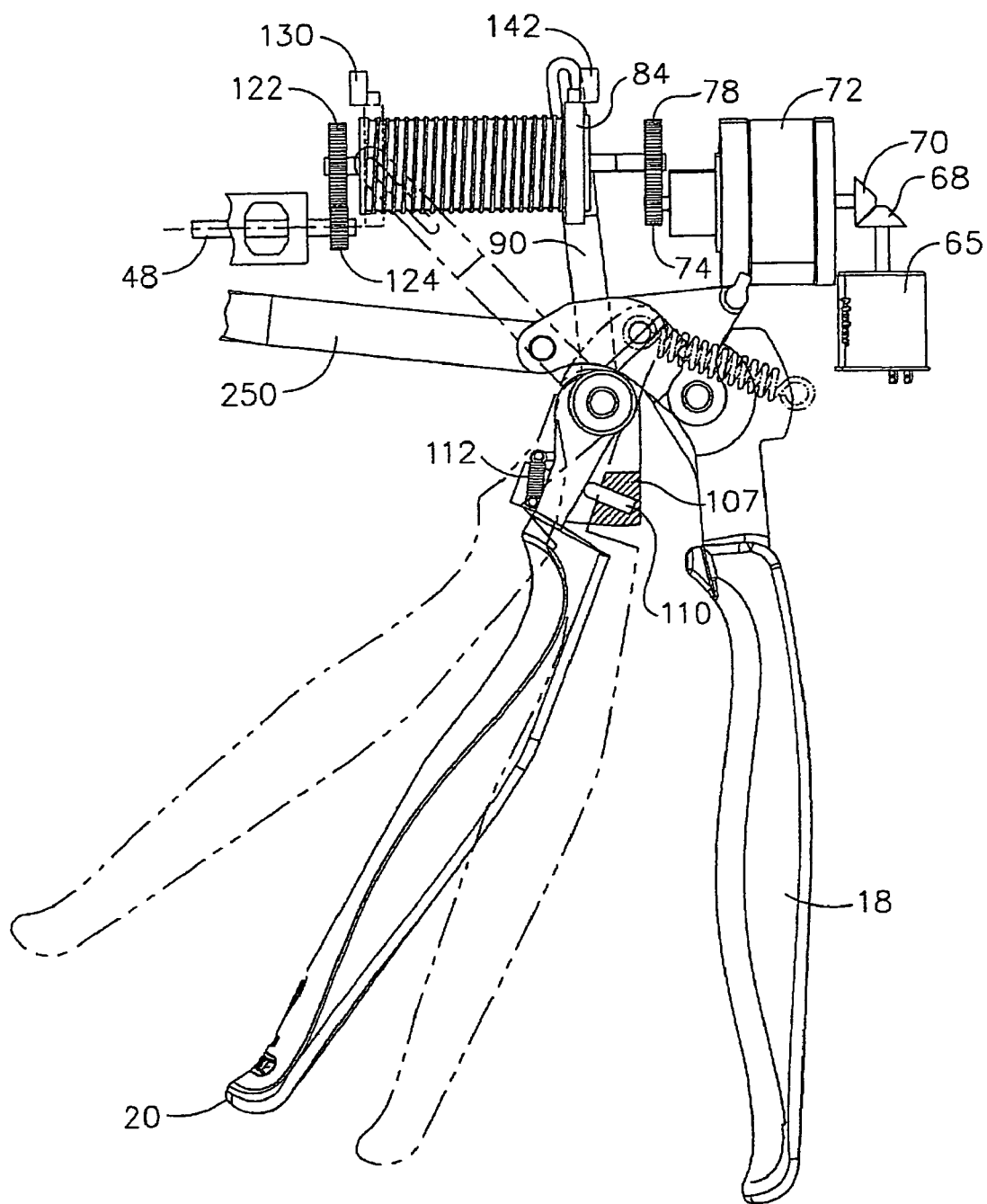
FIG. 10 is a side view of the handle according to various embodiments of the present invention.

The middle handle piece 104 includes a backside shoulder 106 that engages the slotted arm 90 as best shown in FIGS. 8 and 9. The middle handle piece 104 also has a forward motion stop 107 that engages the firing trigger 20. The movement of the slotted arm 90 is controlled, as explained above, by rotation of the motor 65. When the slotted arm 90 rotates CCW as the ring 84 travels from the proximate end of the helical gear drum 80 to the distal end, the middle handle piece 104 will be free to rotate CCW. Thus, as the user draws in the firing trigger 20, the firing trigger 20 will engage the forward motion stop 107 of the middle handle piece 104, causing the middle handle piece 104 to rotate CCW. Due to the backside shoulder 106 engaging the slotted arm 90, however, the middle handle piece 104 will only be able to rotate CCW as far as the slotted arm 90 permits. In that way, if the motor 65 should stop rotating for some reason, the slotted arm 90 will stop rotating, and the user will not be able to further draw in the firing trigger 20 because the middle handle piece 104 will not be free to rotate CCW due to the slotted arm 90.

Components of an exemplary closure system for closing (or clamping) the anvil 24 of the end effector 12 by retracting the closure trigger 18 are also shown in FIGS. 7-10. In the illustrated embodiment, the closure system includes a yoke 250 connected to the closure trigger 18 by a pin 251 that is inserted through aligned openings in both the closure trigger 18 and the yoke 250. A pivot pin 252, about which the closure trigger 18 pivots, is inserted through another opening in the closure trigger 18 which is offset from where the pin 251 is inserted through the closure trigger 18. Thus, retraction of the closure trigger 18 causes the upper part of the closure trigger 18, to which the yoke 250 is attached via the pin 251, to rotate CCW. The distal end of the yoke 250 is connected, via a pin 254, to a first closure bracket 256. The first closure bracket 256 connects to a second closure bracket 258. Collectively, the closure brackets 256, 258 define an opening in which the proximate end of the proximate closure tube 40 (see FIG. 4) is seated and held such that longitudinal movement of the closure brackets 256, 258 causes longitudinal motion by the proximate closure tube 40. The instrument 10 also includes a closure rod 260 disposed inside the proximate closure tube 40. The closure rod 260 may include a window 261 into which a post 263 on one of the handle exterior pieces, such as exterior lower side piece 59 in the illustrated embodiment, is disposed to fixedly connect the closure rod 260 to the handle 6. In that way, the proximate closure tube 40 is capable of moving longitudinally relative to the closure rod 260. The closure rod 260 may also include a distal collar 267 that fits into a cavity 269 in proximate spine tube 46 and is retained therein by a cap 271 (see FIG. 4).

In operation, when the yoke 250 rotates due to retraction of the closure trigger 18, the closure brackets 256, 258 cause the proximate closure tube 40 to move distally (i.e., away from the handle end of the instrument 10), which causes the distal closure tube 42 to move distally, which causes the anvil 24 to rotate about the pivot point 25 into the clamped or closed position. When the closure trigger 18 is unlocked from the locked position, the proximate closure tube 40 is caused to slide proximately, which causes the distal closure tube 42 to slide proximately, which, by virtue of the tab 27 being inserted in the window 45 of the distal closure tube 42, causes the anvil 24 to pivot about the pivot point 25 into the open or unclamped position. In that way, by retracting and locking the closure trigger 18, an operator may clamp tissue between the anvil 24 and channel 22, and may unclamp the tissue following the cutting/stapling operation by unlocking the closure trigger 18 from the locked position.

The control unit (described further below) may receive the outputs from end-of-stroke and beginning-of-stroke sensors 130, 142 and the run-motor sensor 110, and may control the motor 65 based on the inputs. For example, when an operator initially pulls the firing trigger 20 after locking the closure trigger 18, the run-motor sensor 110 is actuated. If the staple cartridge 34 is present in the end effector 12, a cartridge lockout sensor (not shown) may be closed, in which case the control unit may output a control signal to the motor 65 to cause the motor 65 to rotate in the forward direction. When the end effector 12 reaches the end of its stroke, the reverse motor sensor 130 will be activated. The control unit may receive this output from the reverse motor sensor 130 and cause the motor 65 to reverse its rotational direction. When the knife 32 is fully retracted, the stop motor sensor switch 142 is activated, causing the control unit to stop the motor 65.

In other embodiments, rather than a proportional-type sensor 110, an on-off type sensor could be used. In such embodiments, the rate of rotation of the motor 65 would not be proportional to the force applied by the operator. Rather, the motor 65 would generally rotate at a constant rate. But the operator would still experience force feedback because the firing trigger 20 is geared into the gear drive train.

Figure 11:
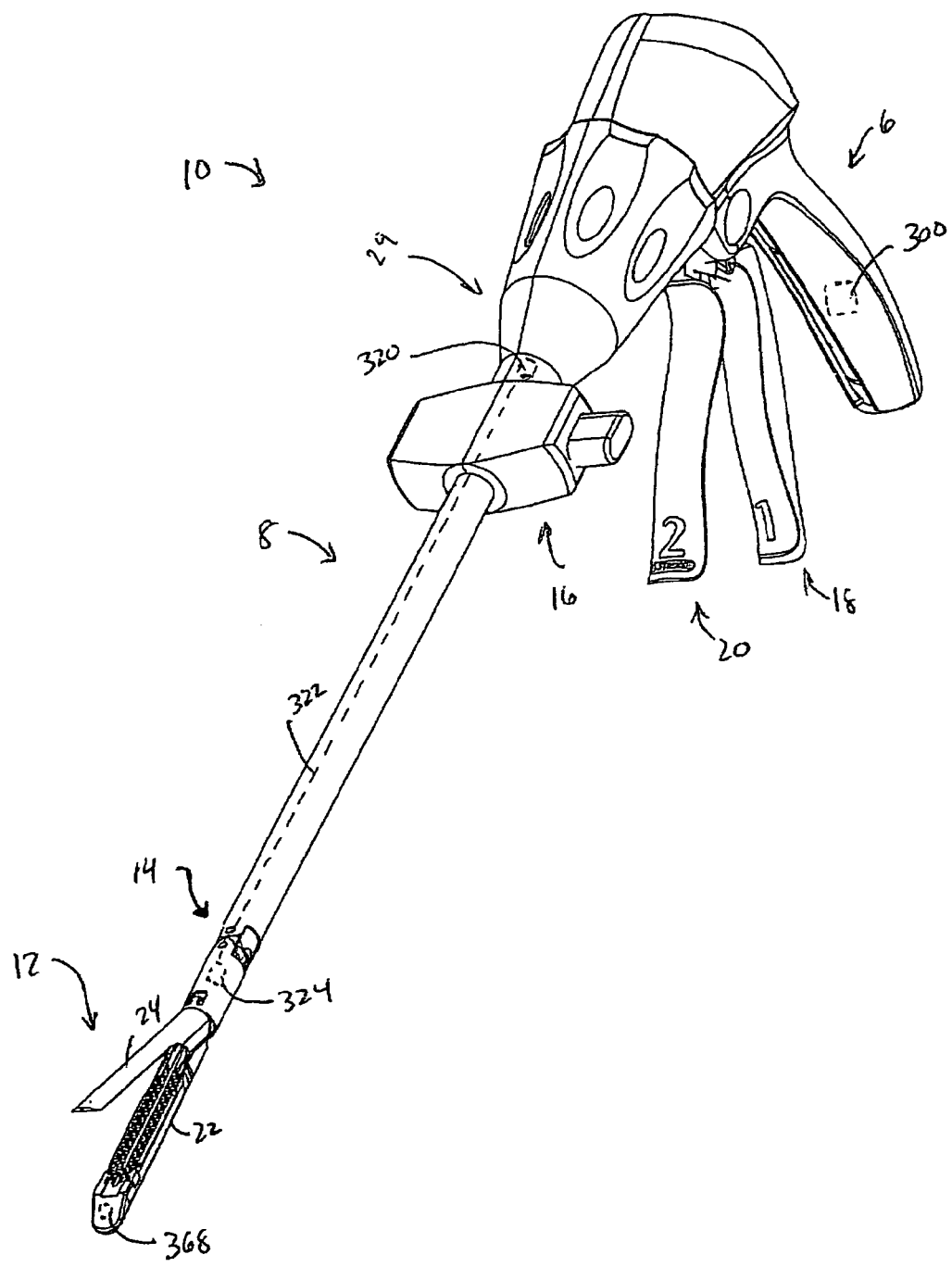
FIG. 11 is a perspective view of a surgical instrument according to various embodiments of the present invention.

The instrument 10 may include a number of sensors in the end effector 12 for sensing various conditions related to the end effector 12, such as sensors for determining the status of the staple cartridge 34 (or other type of cartridge depending on the type of surgical instrument), user input loads, the progress of the stapler during closure and firing, a compatible surgical instrument or instruments for the cartridge 34, etc. The sensors may be passively powered by inductive signals, or may be powered by a remote power source, such as a battery in the end effector 12, for example. The sensor(s) could include magnetoresistive, optical, electromechanical, radio frequency identification (RFID), micro-electrical-mechanical systems (MEMS), motion or pressure sensors, for example. These sensors may be in communication with a control unit 300, which may be located in the handle 6 of the instrument 10, for example, as shown in FIG. 11. The sensors may be in contact with the control unit 300 according to any suitable wired or wireless method.

Figure 12:
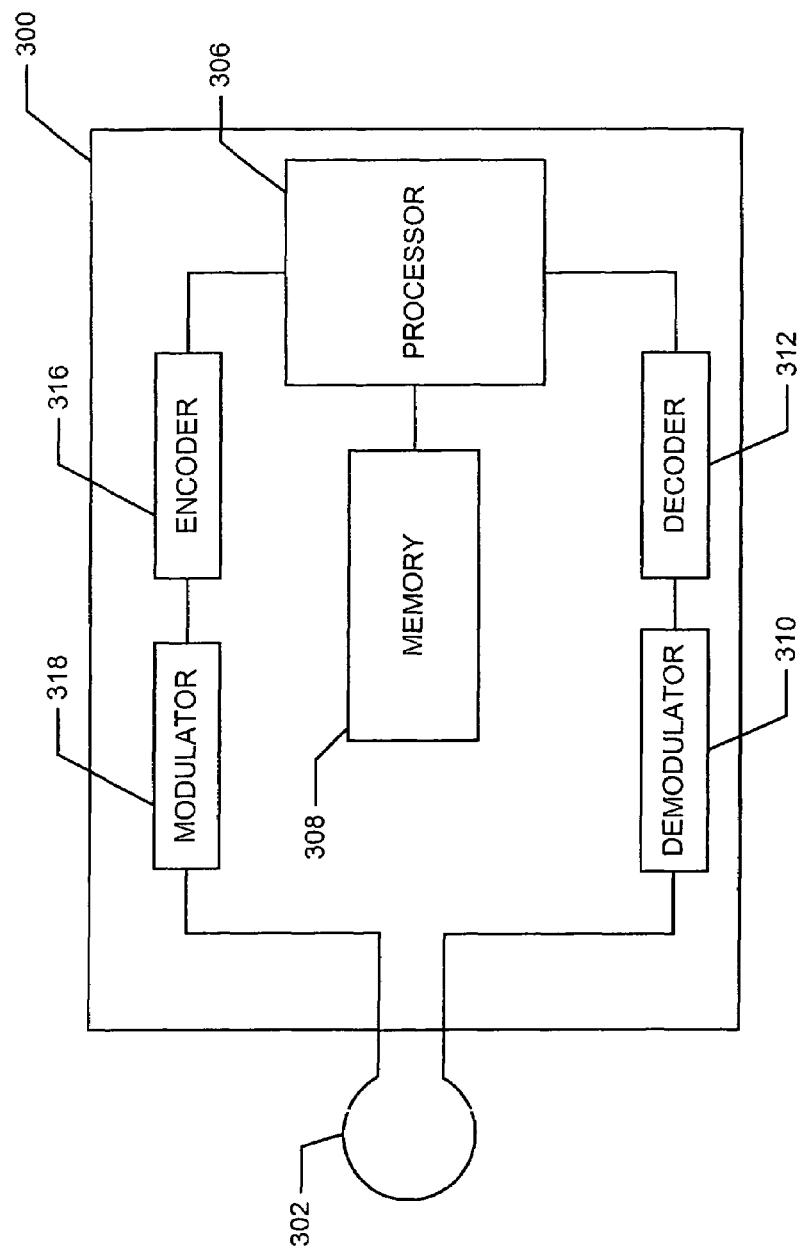
FIG. 12 is a schematic diagram of a circuit used in the instrument according to various embodiments of the present invention.

As shown in FIG. 12, according to various embodiments, the control unit 300 may comprise a processor 306 and one or more memory units 308. By executing instruction codes stored in the memory 308, the processor 306 may control various components of the instrument 10, such as the motor 65 or a user display (not shown), based on inputs received from the various end effector sensors and other sensor(s) (such as the run-motor sensor 110, the end-of-stroke sensor 130, and the beginning-of-stroke sensor 142, for example). The control unit 300 may be powered by the battery 64 during surgical use of instrument 10. In embodiments where the control unit 300 does not have a direct, wired connection to each of the sensors and/or motors, it may comprise an inductive element 302 (e.g., a coil or antenna) for transmitting and receiving wireless signals from the various sensors/motors, etc. Input signals received by the inductive element 302 acting as a receiving antenna may be demodulated by a demodulator 310 and decoded by a decoder 312. Output signals may be transmitted via the encoder 316, modulator 318 and inductive element 302. Various embodiments may include separate inductive elements (not shown) for receiving and transmitting.

According to various embodiments, the control unit 300 may be embodied as a single component, such as a microcontroller, a system-on-chip (SoC) or a system-in-package (SIP). Alternatively, the control unit 300 may be embodied as two or more discrete components. As shown in FIG. 11, the control unit 300 may be housed in the handle 6 of the instrument 10 and one or more of the sensors 368 for the instrument 10 may be located in the end effector 12. In embodiments where the control unit 300 and sensors 368 communicate wirelessly, the inductive element 302 of the control unit 300 may be inductively to the transponders via one or more wires (e.g., 322) and/or secondary inductive elements (e.g., coils 320 and 324). The secondary inductive elements 320, 324 may be placed to avoid running wires through articulating joints such as rotatary joint 29, pivot 14, etc.

Figure 13:
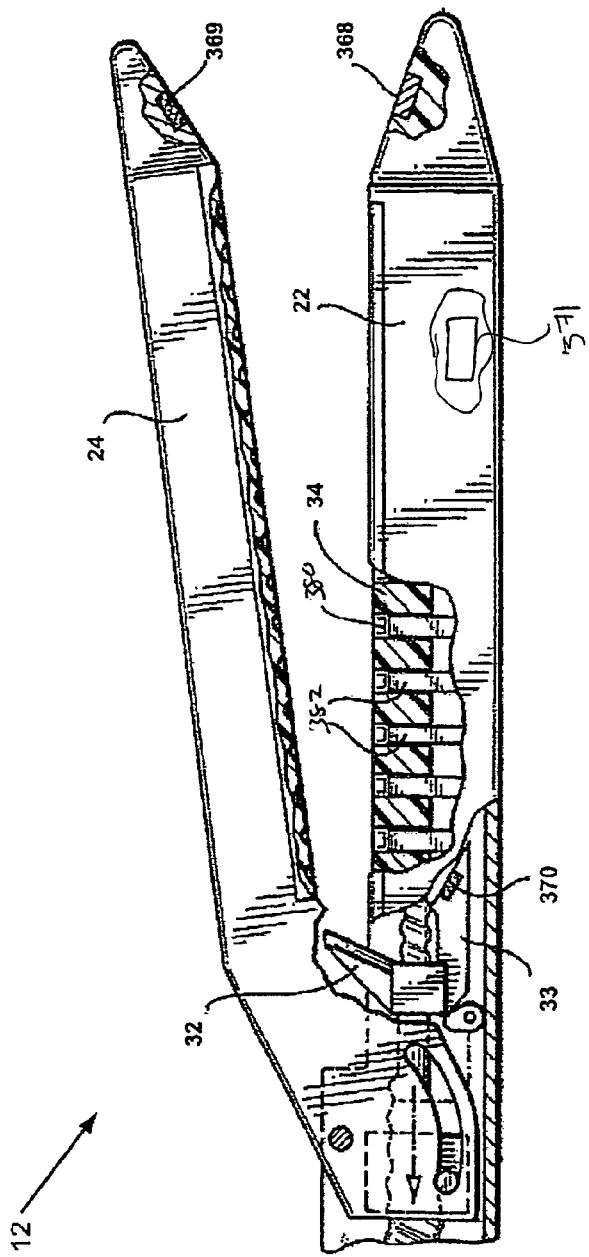
FIG. 13 is a side view of an end effector used in the instrument according to various embodiments of the present invention.

FIG. 13 is a diagram of an end effector 12 including a sensor 368 held or embedded in the cartridge 34 at the distal end of the channel 22. The sensor 368 may be connected to the cartridge 34 by a suitable bonding material, such as epoxy. In this embodiment, the sensor 368 includes a magnetoresistive sensor. The anvil 24 also includes a permanent magnet 369 at its distal end and generally facing the transponder 368. The cartridge 34 also includes a permanent magnet 370 connected to the sled 33 in this example embodiment. This allows the sensor 368 to detect both opening/closing of the end effector 12 (due to the permanent magnet 369 moving further or closer to the transponder as the anvil 24 opens and closes) and completion of the stapling/cutting operation (due to the permanent magnet 370 moving toward the transponder 368 as the sled 33 traverses the channel 22 as part of the cutting operation). It will be appreciated that various other sensors and/or sensor types may be included in the end effector 12 and/or cartridge 34 including, for example, the radio frequency identification (RFID) sensor 371 shown.

FIG. 13 also shows the staples 380 and the staple drivers 382 of the staple cartridge 34. As explained previously, according to various embodiments, when the sled 33 traverses the channel 22, the sled 33 drives the staple drivers 382 which drive the staples 380 into the severed tissue held in the end effector 12, the staples 380 being formed against the anvil 24. As noted above, such a surgical cutting and fastening instrument is but one type of surgical instrument in which the present invention may be advantageously employed. Various embodiments of the present invention may be used in any type of surgical instrument having one or more sensors.

In the embodiments described above, the battery 64 or other suitable power source powers (at least partially) the firing operation of the instrument 10. As such, the instrument may be a so-called "power-assist" device. More details and additional embodiments of power-assist devices are described in the '573 application, which is incorporated herein. It should be recognized, however, that the instrument 10 need not be a power-assist device and that this is merely an example of a type of device that may utilize aspects of the present invention. For example, the instrument 10 may include a user display (such as a LCD or LED display) that is powered by the battery 64 and controlled by the control unit 300. Data from the sensor transponders 368 in the end effector 12 may be displayed on such a display.

Typically, surgical instruments, such as the instrument 10, are cleaned and sterilized prior to use. In one sterilization technique, the instrument 10 is placed in a closed and sealed package 280, such as a plastic and/or TYVEK container or bag, as shown in FIGS. 14 and 15. The package 280 and the instrument are then placed in a field of radiation that can penetrate the package, such as gamma radiation, x-rays, or high-energy electrons. The radiation kills bacteria on the instrument 10 and in the package 280. The sterilized instrument 10 can then be stored in the sterile package 280. The sealed, sterile package 280 keeps the instrument 10 sterile until it is opened in a medical facility or some other use environment. Instead of radiation, other means of sterilizing the instrument 10 may be used, such as ethylene oxide or steam. The instrument 10 may be provided to a customer in a sterilized or un-sterilized state. When the instrument 10 is provided in an un-sterilized state, the customer may sterilize the instrument 10 in-house, or send it out to an outside contractor.

Figure 16:
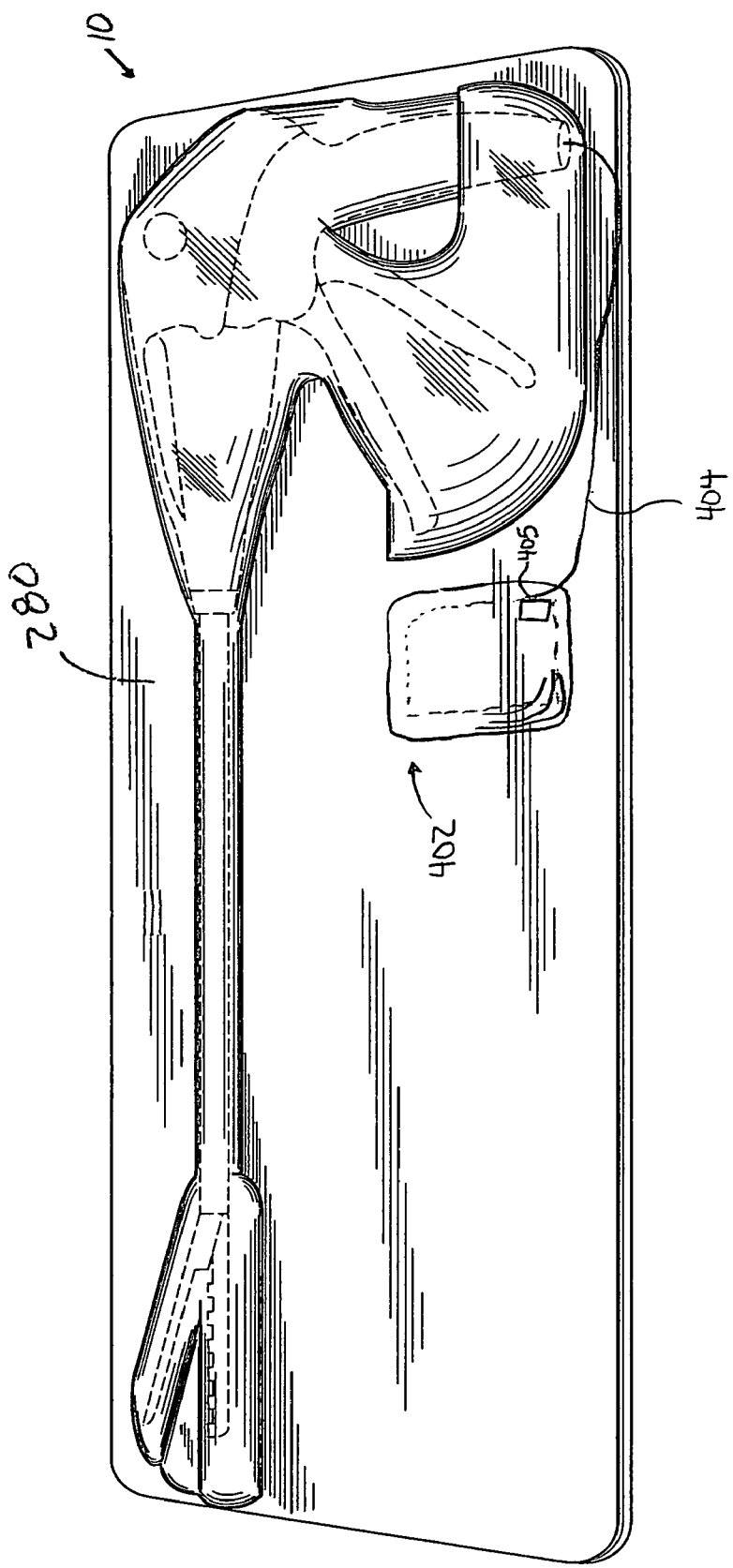

FIG. 16 shows a view, according to various embodiments, of the instrument 10 and package 280 that also includes an auxiliary power source 402. The auxiliary power source 402 may be in electrical communication with the instrument 10 (e.g., the battery 64) via a connection 404 and a circuit element (not shown). The auxiliary power source 402 may provide power for charging and/or recharging an instrument power source. The auxiliary power source 402 may be any kind of battery or other suitable power source. For example, the auxiliary power source may include a rechargeable battery, such as a lithium-ion or nickel metal hydride battery, a non-rechargeable battery, such as a Zinc/Carbon, Zn/alkaline/$MnO_2$, $Li/MnO_2$, $Zn/Ag2O$, $Li/FeS_2$, etc.

The circuit element may regulate power transferred from the auxiliary power source 402 to the instrument 10 to ensure that the battery 64 or other power source of the instrument 10 has an appropriate charge when the instrument 10 is ready for use. Physically, the circuit element may be positioned in any suitable location including, for example, as a stand alone item within the package 280, within the auxiliary power source 402, within the instrument, etc. The connection 404 may be any suitable kind of connection including, for example, a direct wired connection, an inductive connection, etc. In an inductive connection, the connection 404 may include inductive elements in close proximity to one another. A current in a first inductive element may induce a corresponding current in a second inductive element, thus transferring electric power across the connection 404.

Figure 17:
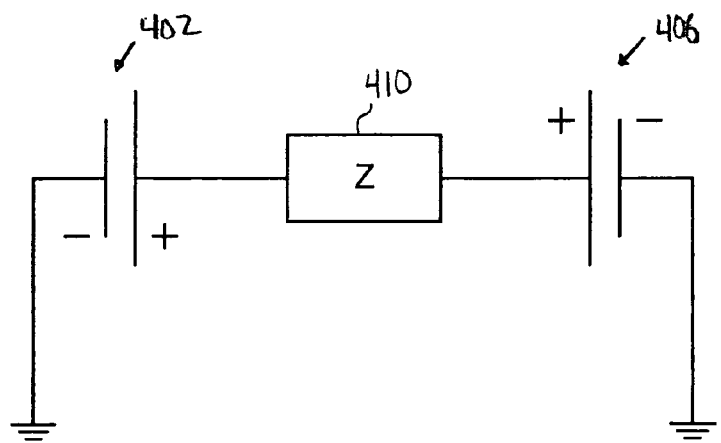
FIGS. 17-19 show schematic diagrams of circuits used in the instrument according to various embodiments of the present invention.
Figure 18:
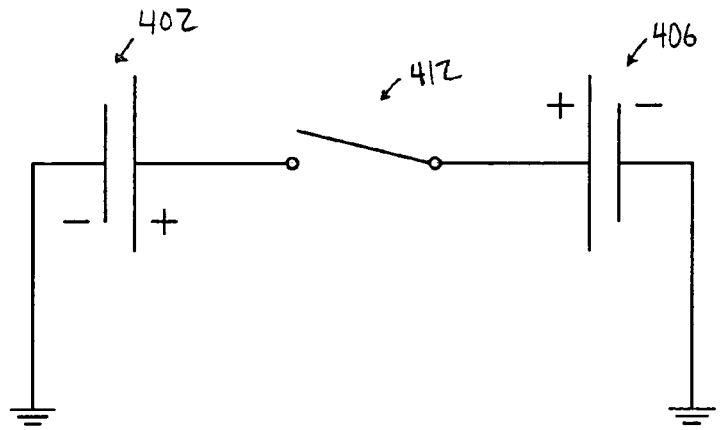
Figure 19:
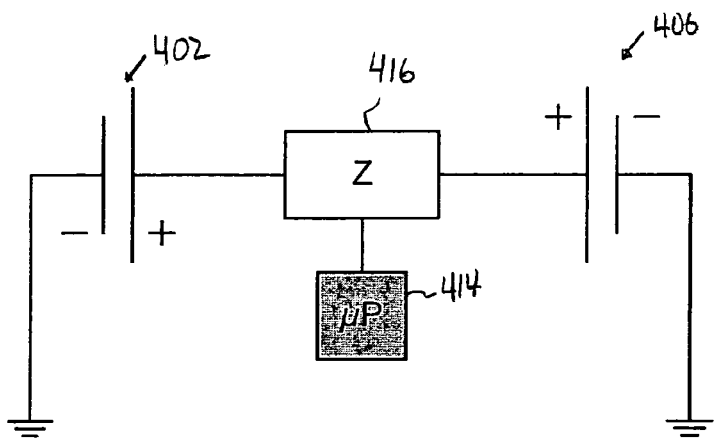

FIG. 17 shows an exemplary schematic diagram of the auxiliary power source 402 connected to an instrument power source 406 (e.g., battery 64) via a circuit element 410. The auxiliary power source 402 may charge the instrument power source 406 according to any suitable method or charging profile. For example, the circuit element 410 may comprise a direct connection (e.g., inductive or wired) between the power sources 402, 406. The auxiliary source 402 may provide a charging current to charge the instrument source 406 as its charge is dissipated, for example, as the instrument 10 sits on the shelf. Also, for example, the auxiliary power source 402 may provide a charging current based on a current state of the source instrument. As shown in FIG. 18, the circuit element 410 may comprise one or more switches 412 or resistors (not shown) to monitor the charge on the instrument power source 406 and provide current from the auxiliary source 402 when the charge on the source 406 reaches a predetermined threshold. Current provided by the auxiliary power source 402 may also be regulated by various other means including, for example, by microprocessor 414 and switch network 416 as shown in FIG. 19. The functions of the processor 414 may be performed by the processor 306 described above, or by any other control system of the instrument 10.

According to various embodiments, the auxiliary power source 402 may charge the instrument source 406 relatively quickly when the instrument 10 is ready for use. For example, referring to FIG. 18, the switch 412 may be left in an open position while the instrument 10 and package 280 are stocked. Accordingly, the charge on the instrument power source 406 may be allowed to degrade. When the instrument 10 is ready for use, the switch 412 closed, allowing the auxiliary power source 402 to provide a charging current to the power source 406, charging the source 406 prior to use. For example, the switch 412 may be configured to close automatically when the package 280 is opened. In various embodiments, the switch may include a tab 405, as shown in FIG. 16.

The tab 405 may be connected to a portion of the package 280 and configured to close the switch 412 as the package 280 is opened. Also, for example, a clinician may pull the tab 405 at or near the time when the instrument 10 will be used, closing the switch 412 and causing the source 406 to charge.

Figure 20:
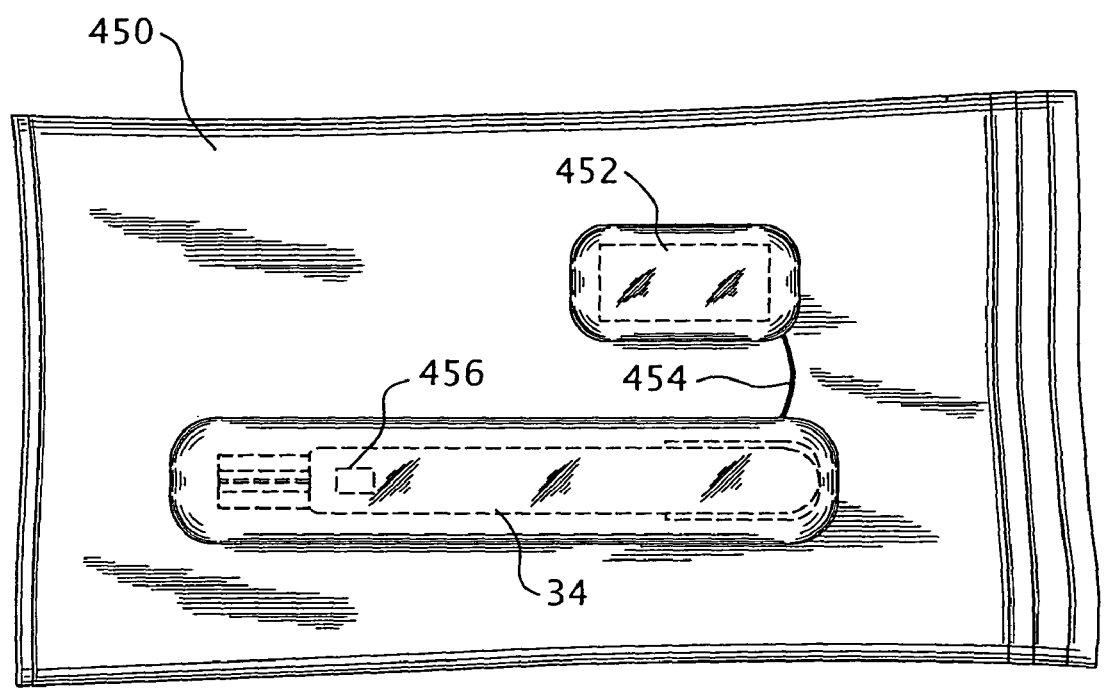
FIG. 20 shows a component of the instrument in a sterile package according to various embodiments of the present invention.
Figure 21:
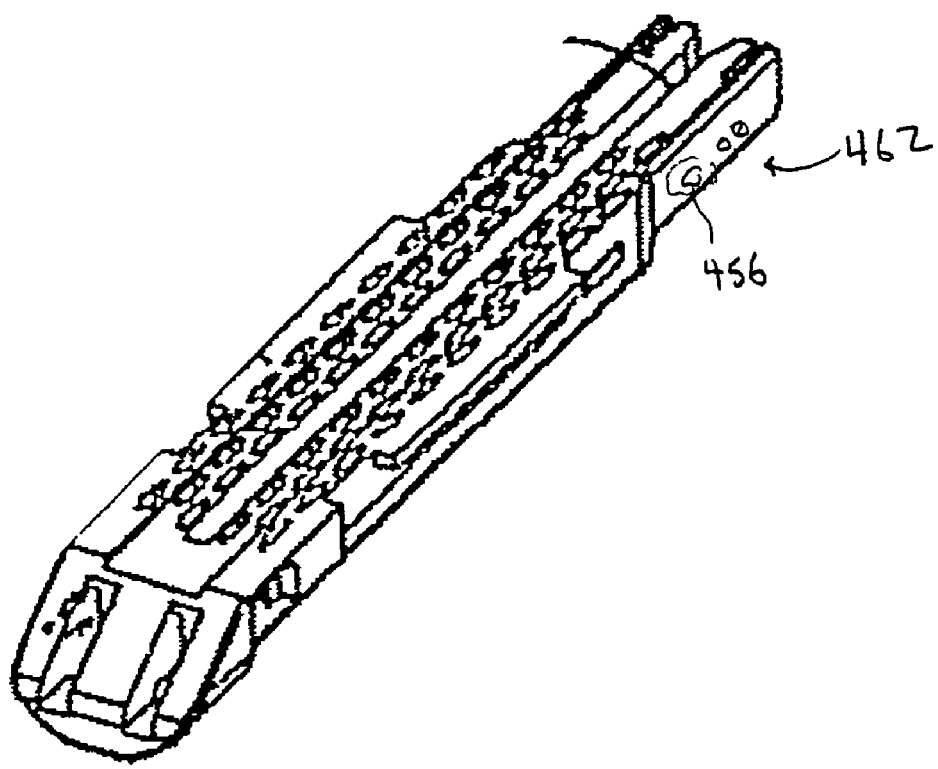
FIG. 21 shows a component of the instrument according to various embodiments of the present invention.

As described above, some end effector cartridges 34 may have sensors or other electrical components that require a power source. For example, FIG. 3 shows the cartridge 34 with a power source 456. The power source 456 may be any power source suitable for operating electronics present in the cartridge and/or the end effector 12. For example, the power source 456 may include a capacitor, a battery, etc. The power source 456 may be positioned within the cartridge 34 in any suitable location including, for example, at a distal tip, as shown in FIG. 20, and as a part of the sled 33, as shown in FIG. 21.

End effector cartridges 34 may be stored and sterilized according to the methods described above. For example, FIG. 20 shows a view of a cartridge 34 enclosed in a package 450 for sterilization. As shown, the package 450 also includes an auxiliary power source 452. The auxiliary power source may provide power to the cartridge power source 456. Like the power source 402, the power source 452 may tend to charge or recharge a power source 456 of the cartridge 34, thus increasing the shelf-life of the cartridge 34. The auxiliary power source 452 may be linked to the cartridge 34 via a connection 454 and a circuit element (not shown) similar to the circuit element described above. The auxiliary power source 452, circuit element and cartridge power source may be linked and may charge the power source 456 according to any suitable method wired or wireless (e.g., inductive) method including, for example, those discussed above with respect to FIGS. 17, 18 and 19.

According to various embodiments, a cartridge power source 456 may have a small charge capacity. Accordingly, it may be desirable to prevent unnecessary use of this charge. For example, the cartridge power source 456 may be electrically isolated from its load until the cartridge 34 is ready for use. The cartridge 34 may include a cut-off switch or other circuit element that is closed when the cartridge 34 is installed in an end effector 12. When the cut-off switch is closed, the power source 456 may be connected to its load (e.g., any sensors or other powered electronics present in the cartridge 34).

The cut-off switch may be implemented in any suitable way. For example, as shown in FIG. 3, the cartridge 34 may include indentations 401 that are received by corresponding protrusions (not shown) in the channel 22 when the cartridge 34 is secured into the channel 22. Switch elements may be placed within these indentations 401. When the cartridge 34 is installed into the channel 22, the protrusions may be received into the indentations 401, closing the cut-off switch and connecting the power source 456 to its load. FIG. 21 shows an additional embodiment of the cut-off switch. As shown, the cut-off switch may include a pair of electrical contacts 462 positioned on a sidewall of the cartridge 34. When the cartridge 34 is secured within the channel 22 (see FIG. 3), the contacts 462 are shorted by the conductive sidewall of the channel 22, closing the switch and connecting the power source 456 to its load.

The various embodiments of the present invention have been described above in connection with cutting-type surgical instruments. It should be noted, however, that in other embodiments, the inventive surgical instrument disclosed herein need not be a cutting-type surgical instrument, but rather could be used in any type of surgical instrument including remote sensor transponders. For example, it could be a non-cutting endoscopic instrument, a grasper, a stapler, a clip applier, an access device, a drug/gene therapy delivery device, an energy device using ultrasound, RF, laser, etc. In addition, the present invention may be in laparoscopic instruments, for example.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Although the present invention has been described herein in connection with certain disclosed embodiments, many modifications and variations to those embodiments may be implemented. For example, different types of end effectors may be employed. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

We claim:

1. An assembly comprising:
   a package;
   a surgical instrument component within the package;
   a power source within the package, wherein the power source is configured to be placed in electrical communication with the surgical instrument component;
   an auxiliary power source within the package; and
   a switch in electrical communication with the power source and the auxiliary power source, wherein the switch comprises a tab coupled to a portion of the package in a manner causing the switch to be configured to an open position when the package is closed and wherein the tab is also coupled to the package in a manner causing the switch to be transitioned to a closed position automatically when the package is opened.

2. The assembly of claim 1, wherein the package is sterile.

3. The assembly of claim 1, wherein the power source is a battery.

4. The assembly of claim 1, wherein the power source comprises at least one battery cell selected from the group consisting of a lithium ion cell and a nickel metal hydride cell.

5. The assembly of claim 1, wherein the power source is a capacitor.

6. The assembly of claim 1, wherein the surgical instrument component comprises an endocutter.

7. The assembly of claim 1, wherein the surgical instrument component comprises an end effector cartridge for a surgical instrument.

8. The assembly of claim 1, wherein the power source is not in electrical communication with the instrument component.

9. The assembly of claim 1, wherein the auxiliary power source comprises at least one cell selected from the group consisting of a Zinc/Carbon cell, a Zn/alkaline/MnO2 cell, a Li/MnO2 cell, a Zn/Ag2O, and a Li/FeS2 cell.

10. An assembly comprising:
a package;
an end effector cartridge within the package, wherein the end effector cartridge comprises an electrical component;
a power source within the package;
an auxiliary power source within the package;
a switch in electrical communication with the power source and the electrical component, wherein the switch comprises a tab coupled to a portion of the package in a manner causing the switch to be configured to an open position when the package is closed and wherein the tab is also coupled to the package in a manner causing the switch to be transitioned to a closed position automatically when the package is opened; and
a circuit element within the package, wherein the circuit element is in electrical communication with the power source and the electrical component and is configured to electrically connect the power source and the electrical component when the end effector cartridge is installed in a surgical instrument.

11. The assembly of claim 10, wherein the circuit element comprises a direct electrical connection between the power source and the auxiliary power source.

12. The assembly of claim 11, wherein the direct electrical connection comprises an inductive connection.

13. The assembly of claim 10, wherein the circuit element comprises a control circuit configured to regulate electrical communication between the power source and the auxiliary power source.

14. The assembly of claim 10, wherein the control circuit comprises a microprocessor.

15. The assembly of claim 14, wherein the microprocessor is also configured to control at least one component of the surgical instrument when the surgical instrument is in use.

16. The assembly of claim 10, wherein the package is sterile.

17. The end effector cartridge of claim 10, wherein the circuit element comprises a switch configured to close an electrical connection between the electrical component and the power source when the end effector cartridge is installed in the surgical instrument.

* * * * *